US008486697B2

(12) United States Patent
Gudkov et al.

(10) Patent No.: US 8,486,697 B2
(45) Date of Patent: Jul. 16, 2013

(54) INDUCING CELL DEATH BY INHIBITING ADAPTIVE HEAT SHOCK RESPONSE

(75) Inventors: Andrei Gudkov, East Aurora, NY (US); Nickolay Neznanov, Williamsville, NY (US); Katerina Gurova, Orchard Park, NY (US)

(73) Assignees: Incuron, LLC, Buffalo, NY (US); Health Research, Inc., Buffalo, NY (US)

( * ) Notice: Subject to any disclaimer, the term of this patent is extended or adjusted under 35 U.S.C. 154(b) by 254 days.

(21) Appl. No.: 12/993,018

(22) PCT Filed: May 20, 2009

(86) PCT No.: PCT/US2009/044736
§ 371 (c)(1),
(2), (4) Date: Feb. 7, 2011

(87) PCT Pub. No.: WO2009/143290
PCT Pub. Date: Nov. 26, 2009

(65) Prior Publication Data
US 2011/0124104 A1      May 26, 2011

Related U.S. Application Data

(60) Provisional application No. 61/102,913, filed on Oct. 6, 2008, provisional application No. 61/179,674, filed on May 19, 2009, provisional application No. 61/054,785, filed on May 20, 2008.

(51) Int. Cl.
*C12N 5/00* (2006.01)
*C12N 5/02* (2006.01)
*C12N 13/00* (2006.01)

(52) U.S. Cl.
USPC ............... 435/375; 435/6.1; 435/173.1

(58) Field of Classification Search
None
See application file for complete search history.

(56) References Cited

U.S. PATENT DOCUMENTS

| 5,413,587 A | 5/1995 | Hochstein |
| 2002/0058679 A1 | 5/2002 | Yokota et al. |
| 2005/0013778 A1 | 1/2005 | Green et al. |

OTHER PUBLICATIONS

Coss et al. Inhibiting induction of heat shock proteins as a strategy to enhance cancer therapy, Int. J. Hyperthermia, Dec. 2005; 21(8): 695-701.*
Hirsch et al., Nanoshell-mediated near-infrared thermal therapy of tumors under magnetic resonance guidance, PNAS, Nov. 11, 2003, vol. 100, No. 23, 13549-13554.*
Hayess et al., Effect of Protein Kinase Inhibitors on Activity of Mammalian Small Headhock Protein (HSP25) Kinase, Biochemical Pharmacology, vol. 53, 1239-1247, 1997.*
Ishibashi et al., The effects inhibiting the proliferation of cancer cells by far-infrared radiation (FIR) are controlled by the basal expression level of heat shock protein (HSP) 70A, Med Oncol (2008) 25:229-237.*

(Continued)

*Primary Examiner* — James Ketter
*Assistant Examiner* — Reza Ghafoorian
(74) *Attorney, Agent, or Firm* — Polsinelli PC; Teddy C. Scott, Jr.; Ron Galant

(57) ABSTRACT

Provided herein is a method for inducing cell death by inducing heat shock response in a cell in combination with inhibiting adaptive heat shock response. Also provided are methods for preventing cancer, treating intracellular parasite infections, and inflammation-associated conditions.

14 Claims, 23 Drawing Sheets

OTHER PUBLICATIONS

Chauhan et al., Combination of Proteasome Inhibitors Bortezomib and NPI-0052 Trigger in vivo Synergistic Cytotoxicity in Multiple Myeloma. Blood, Feb. 1, 2008 (Available online Nov. 15, 2007) vol. 111, No. 3, pp. 1654-1664.

Kato et al., Enhancement of Stress-Induced Synthesis of Stress Proteins by Mastoparan in C6 Rat Giloma Cells. J. Biochem., Jul. 1995, vol. 118, No. 1, pp. 149-153.

Matsuo et al., Enhanced Expression of the DNA Topoisomerase II Gene in Response to Heat Shock Stress in Human Epidermoid Cancer KB Cells. Cancer Research, Mar. 1, 1993, vol. 53, No. 5, pp. 1085-1090.

Nakamura et al., Antitumor Activity of ER-37328, a Novel Carbazole Topoisomerase II Inhibitor. Molecular Cancer Therapeutics, Jan. 1, 2002, vol. 1, No. 3, pp. 169-175.

* cited by examiner

FIGURE 1
A.
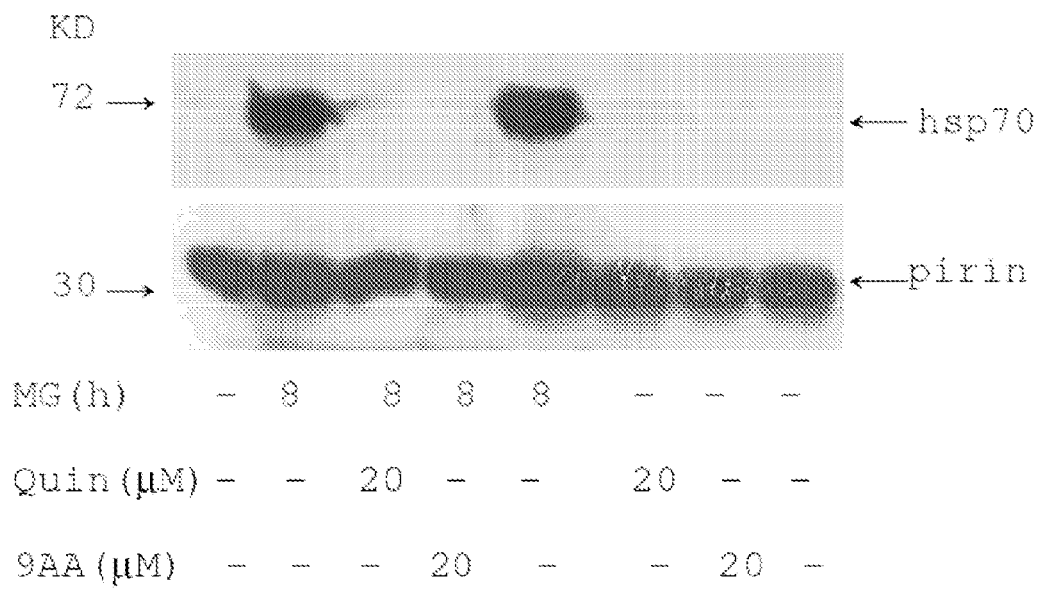
B.
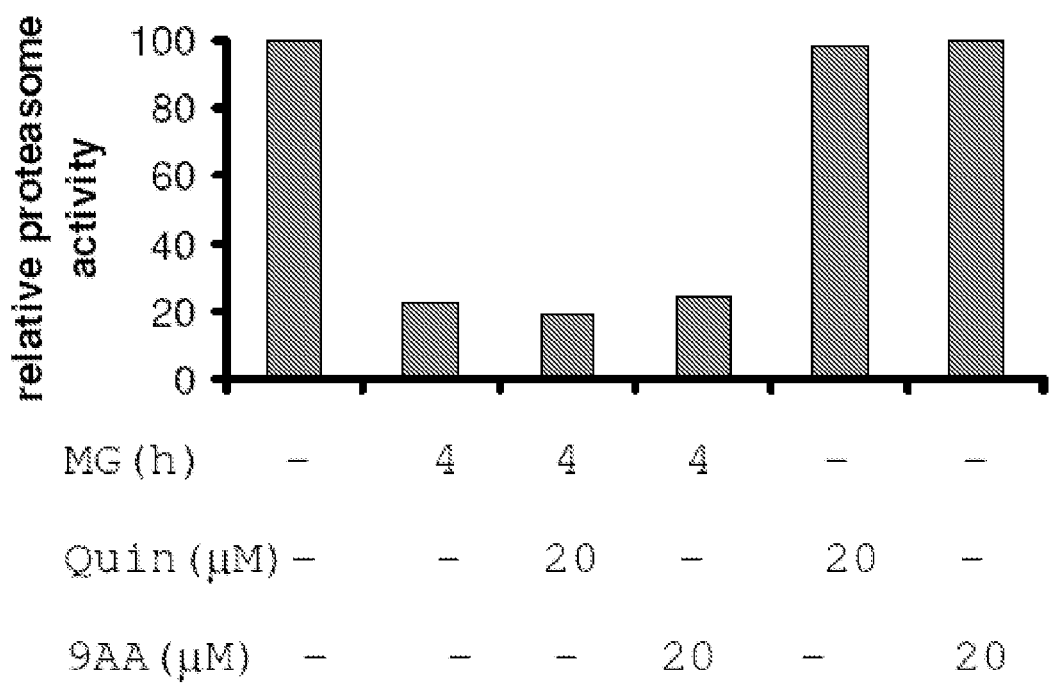

FIGURE 7
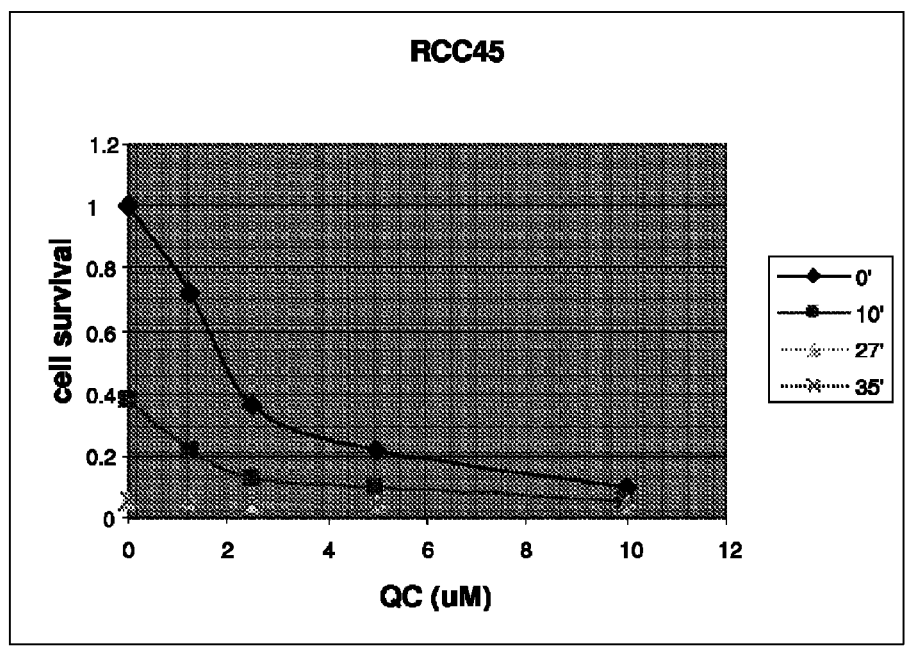
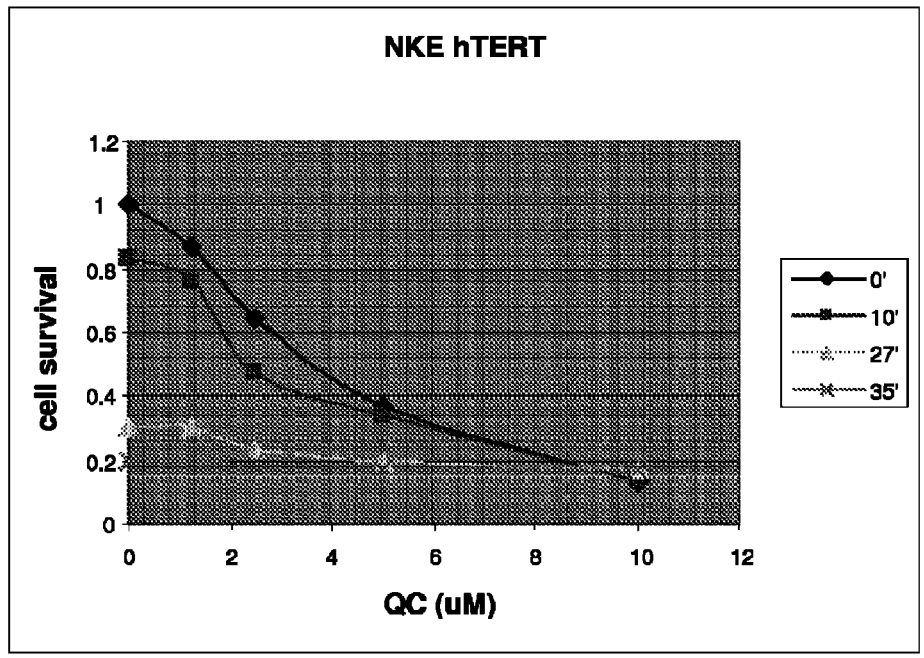

FIGURE 7, Continued
C.
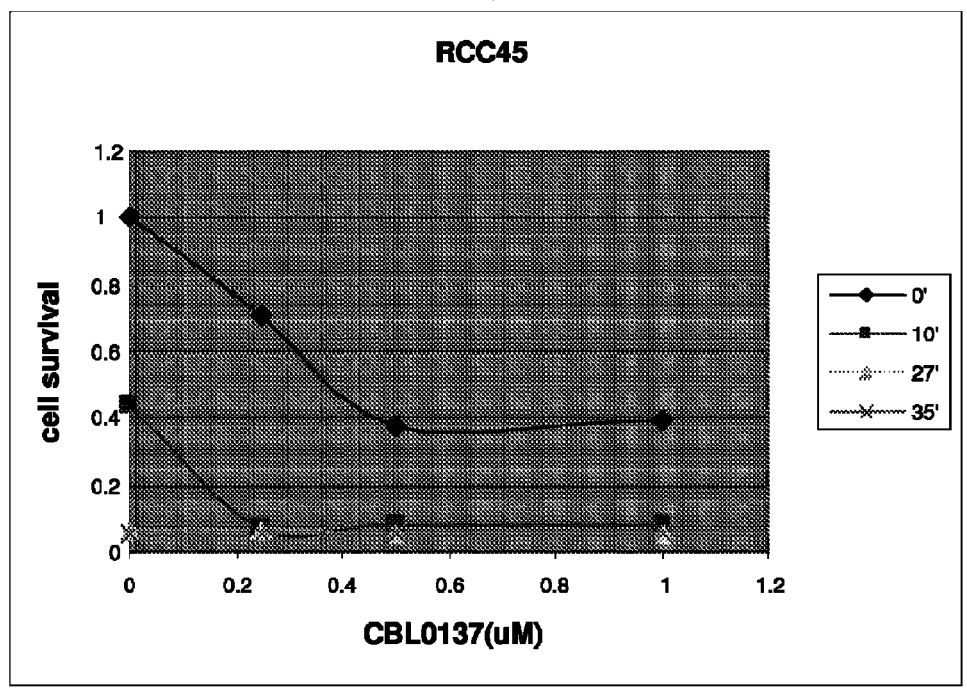
D.
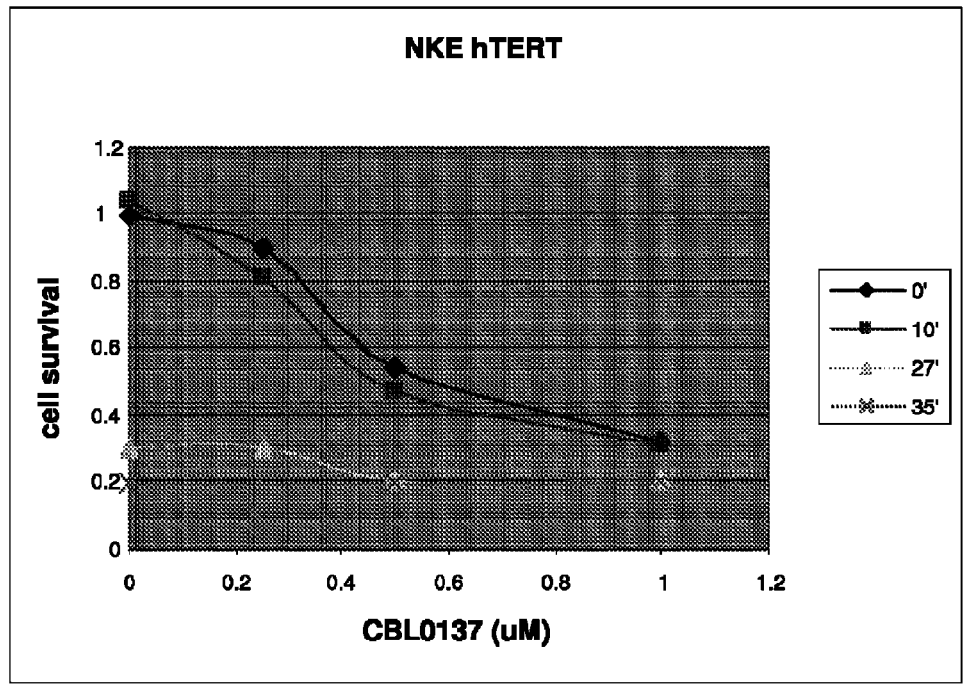

FIGURE 9
A
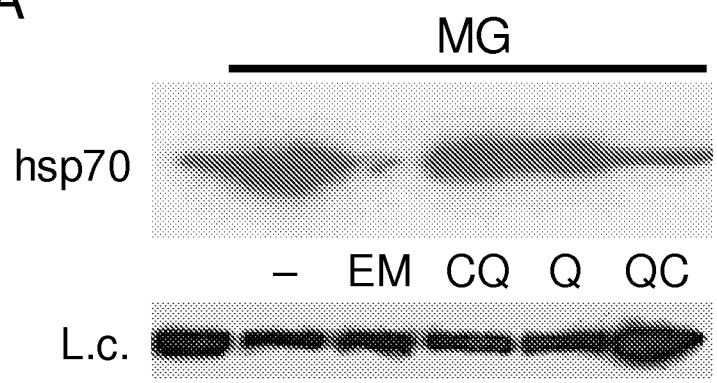
B
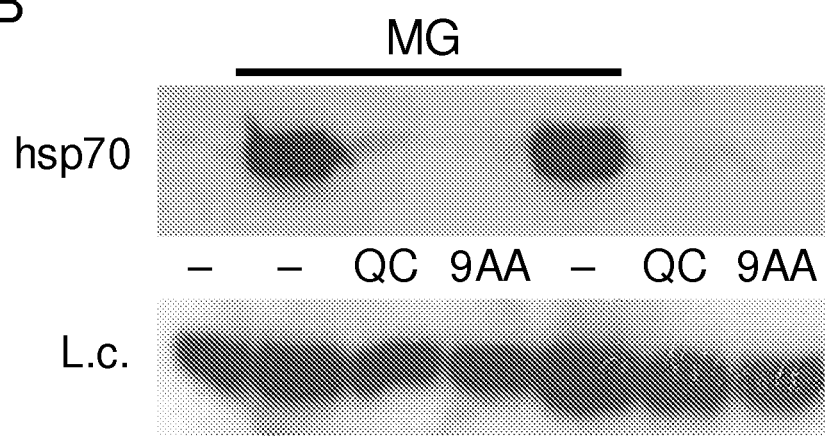
C
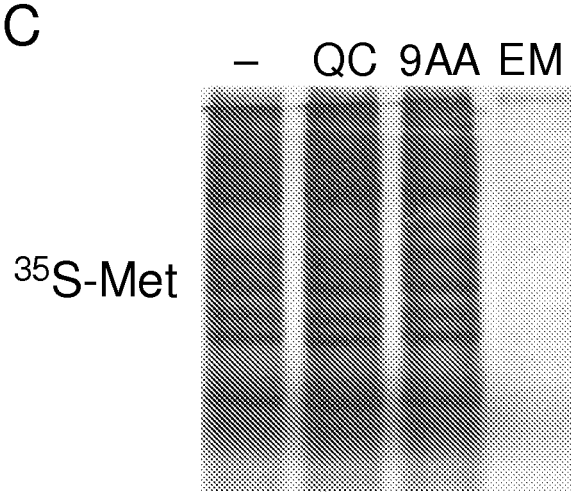

FIGURE 9 (CONTINUED)
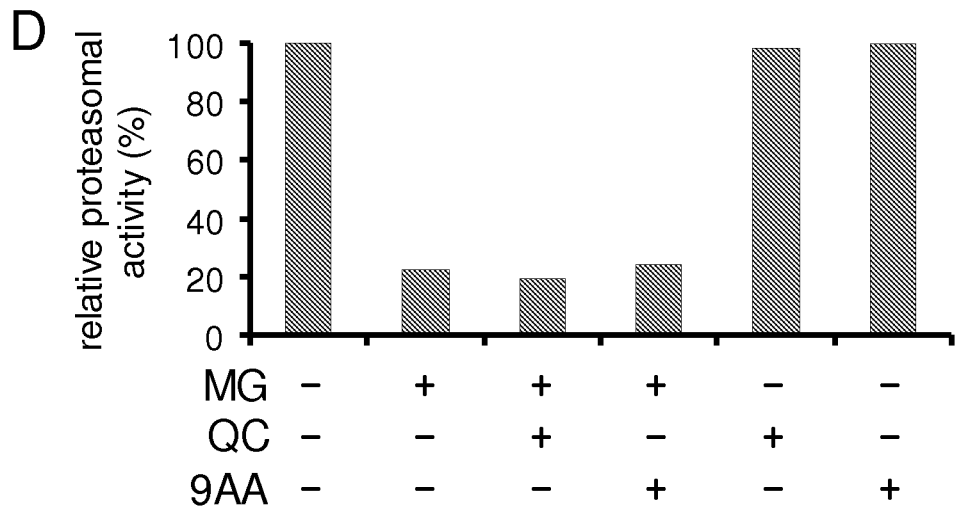
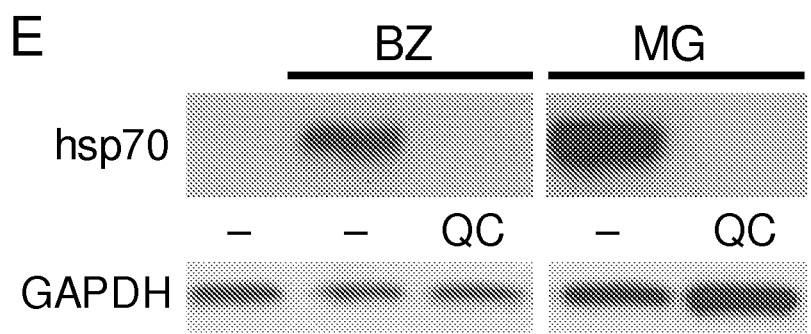
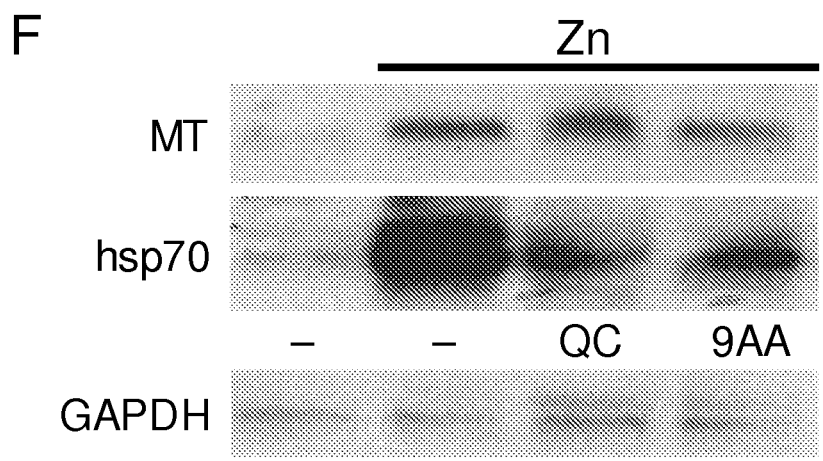

FIGURE 11
A
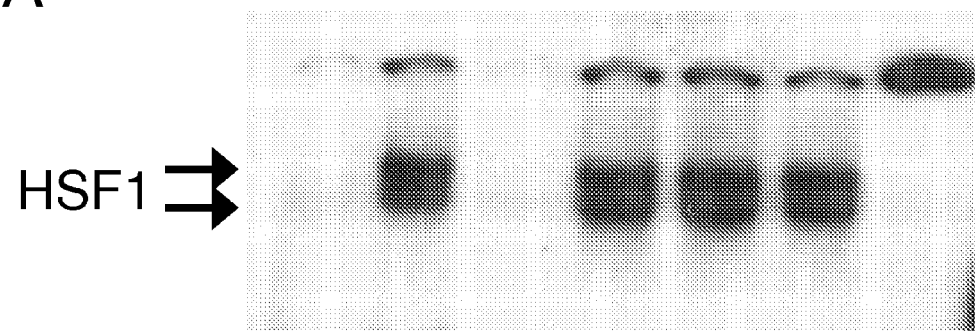
| | | | | | | |
|---|---|---|---|---|---|---|
| MG | − | + | + | + | − | − | + |
| HSF1(50x) | − | − | + | − | − | − | − |
| NFkB(50x) | − | − | − | + | − | − | − |
| HS | − | − | − | − | + | − | − |
| GM | − | − | − | − | − | + | − |
| HSFAbs | − | − | − | − | − | − | + |
B
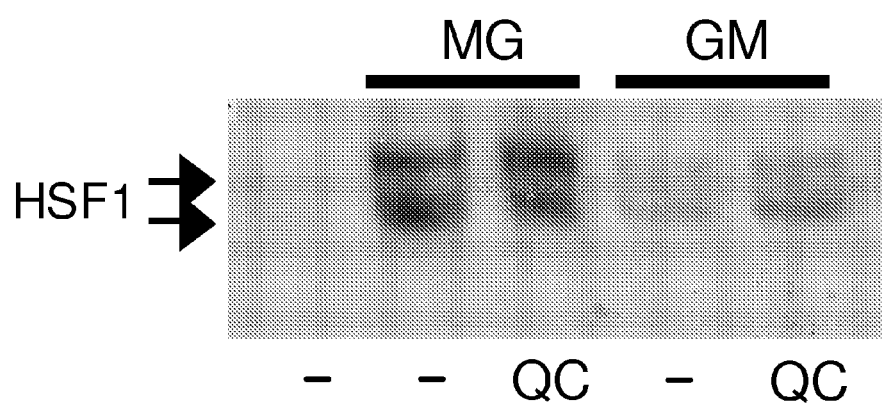

FIGURE 11 (CONTINUED)
C
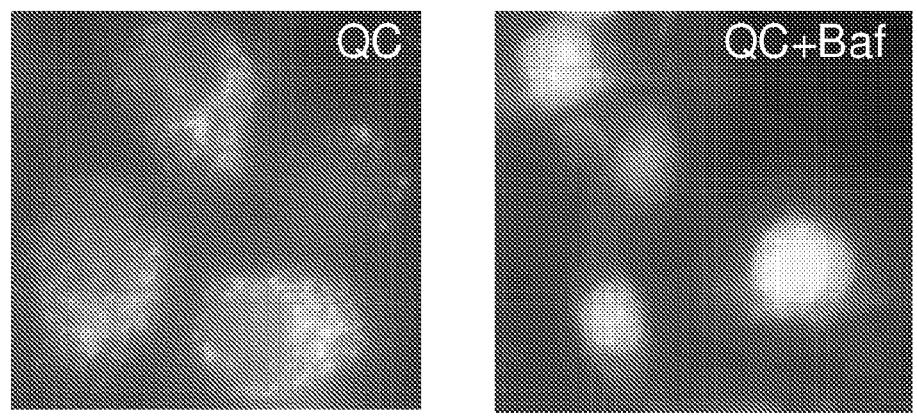
D
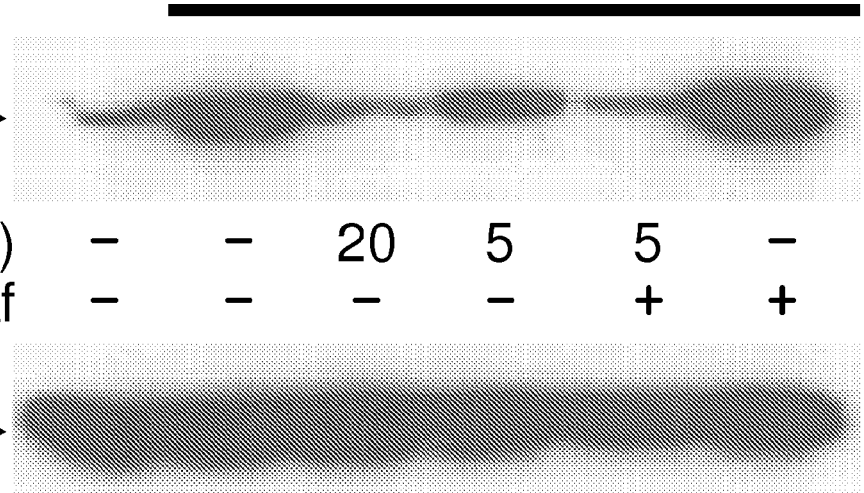

FIGURE 12
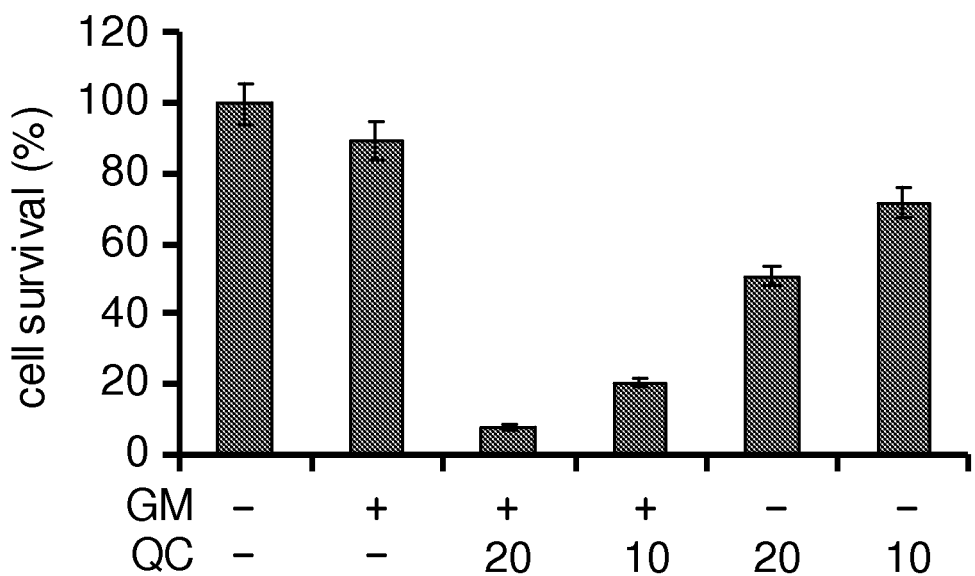
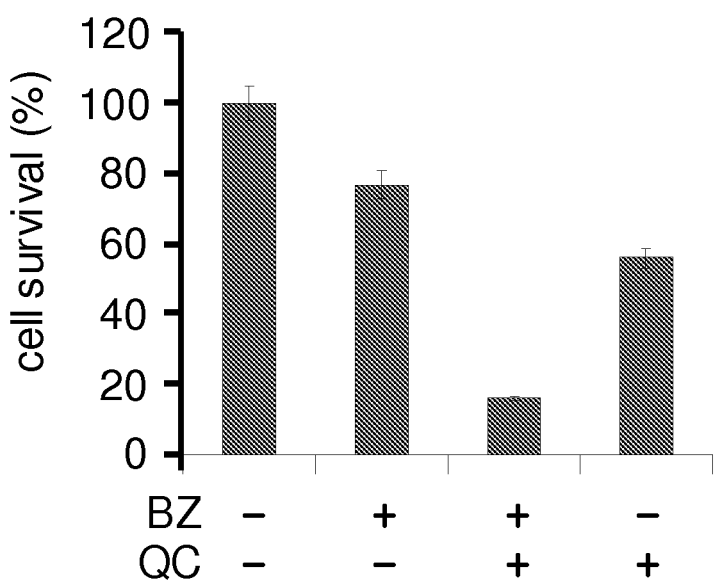

FIGURE 12 (CONTINUED)
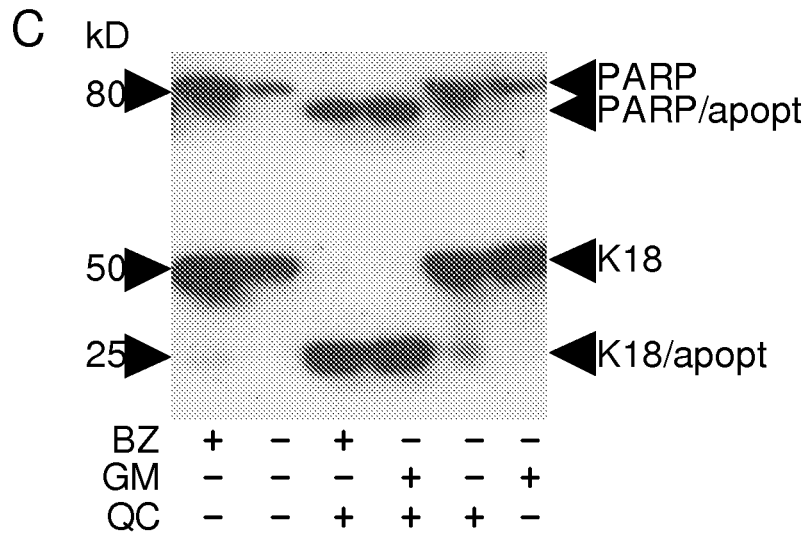
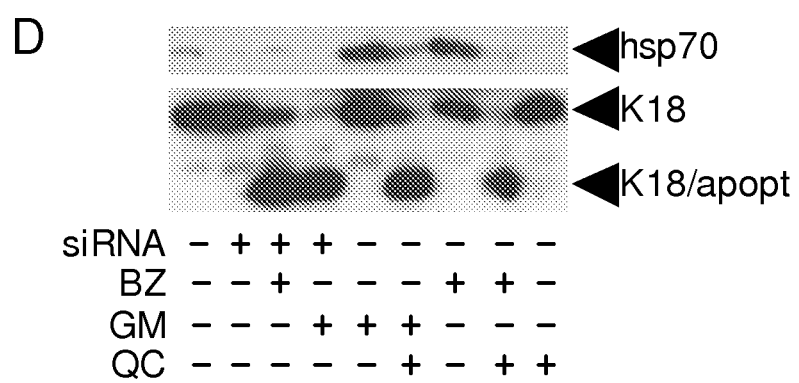
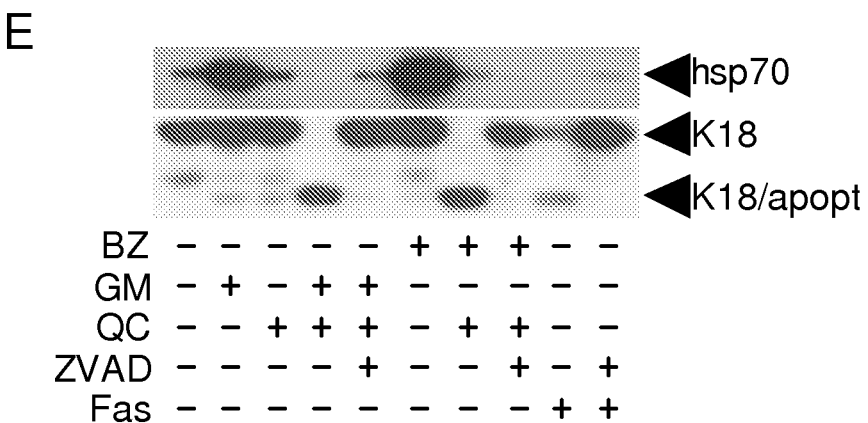

FIGURE 13 (CONTINUED)
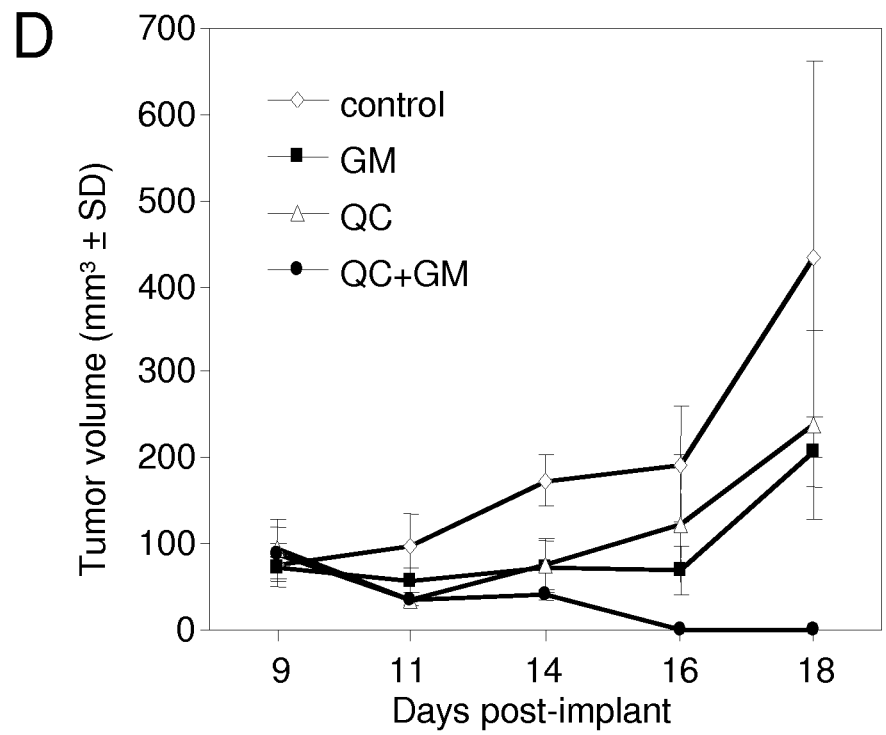
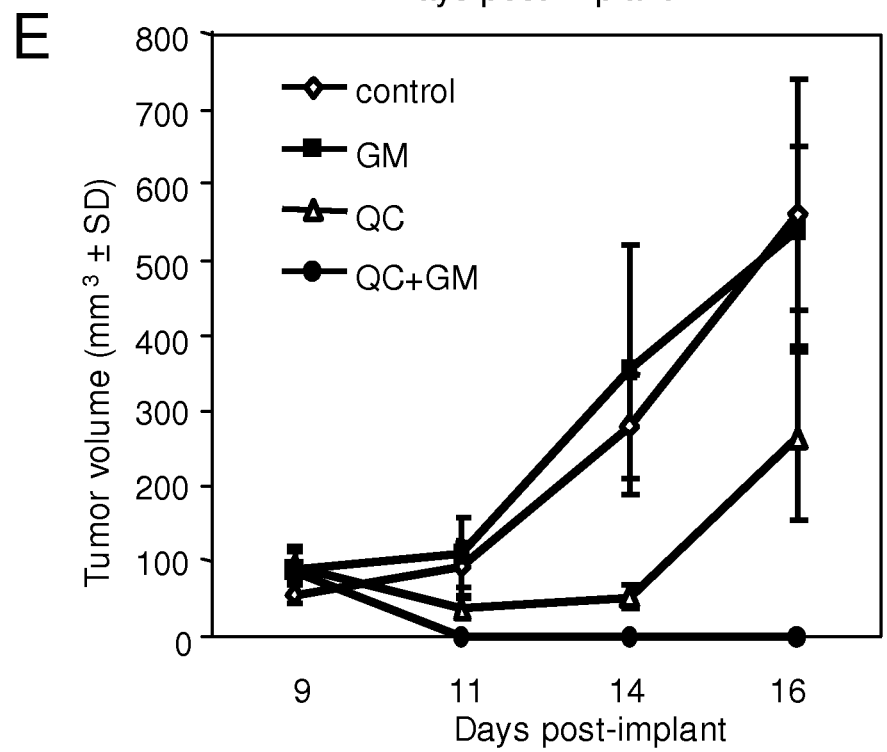

INDUCING CELL DEATH BY INHIBITING ADAPTIVE HEAT SHOCK RESPONSE

CROSS-REFERENCE TO RELATED APPLICATIONS

This is the national stage of International Application No. PCT/US2009/044736, filed on May 20, 2009, which claims the benefit of U.S. Provisional Patent Application No. 61/054,785, filed on May 20, 2008, U.S. Provisional Patent Application No. 61/102,913, filed on Oct. 6, 2008, and U.S. Provisional Patent Application No. 61/179,674 filed on May 19, 2009, the contents of all of which are incorporated herein by reference.

FIELD OF THE INVENTION

This invention is related to a method for inducing cell death by inducing heat shock response in a cell in combination with inhibiting adaptive heat shock response.

BACKGROUND OF THE INVENTION

Cancer is a major public health problem. It accounts for approximately one quarter of all deaths in the United States, and is the leading cause of death among men and women under 85 years of age. The lifetime probability of developing cancer is 46% for men and 38% for women. Many anti-cancer therapies are plagued by side effects including nausea, emesis, hair loss, fever, and risk of infection. Chemotherapy and radiotherapy both lead to high rates of oral and gastrointestinal (GI) mucositis in treated patients, and these effects can be the dose-limiting toxicities of some treatment modalities.

Tumor cells acquire a high level of adaptive heat shock response. The heat shock response is an adaptive mechanism used by all living cellular organisms to survive under the conditions of so-called proteotoxic stress—the condition resulting in accumulation of misfolded proteins, which tend to aggregate leading to cell death due to global protein denaturing triggered by such aggregation. Cells can activate this protective mechanism by inducing synthesis of additional protein chaperones, known as heat shock proteins (HSP).

Tumor cell viability may be dependent on heat shock response because they have higher rate of protein misfolding. However, the efficacy of thermotherapy techniques for cancer are limited by the induction of adaptive heat shock response, which can greatly diminish tumor cell sensitivity to treatment and limit the use of thermotherapy and other heat shock modulating treatments. Accordingly, there is a need for improved methods of inducing cell death.

SUMMARY OF THE INVENTION

Provided herein is a method for inducing cell death, which may comprise inhibiting adaptive heat shock response in a cell and inducing heat shock response in the cell. The heat shock response may be induced by administering a heat shock-inducing agent to the cell. The heat-shock inducing agent may be geldanamycin, a proteasome inhibitor, an arsenite compound, or ethanol. The heat shock response may also be induced by increasing the internal temperature of the cell, which may be performed with a heating means. The temperature may be increased to at least 39-60° C., and may be increased with infrared radiation. The radiation may have a wavelength of 5-15 µm. The temperature may also be increased with a heat source selected from the group consisting of an electroluminescent device, a laser diode, a vertical cavity surface emitting laser, a light emitting diode, and a resistive filament lamp. The inhibitor of adaptive heat shock response may be an aminoacridine, such as quinacrine or 9-aminoacridine, or carbazole.

The cell may be a cancer cell, and the cancer may be selected from the group consisting of: metastatic breast cancer, bladder cancer, lung carcinoma, esophageal cancer, basal cell carcinoma, malignant melanoma, ocular tumor, and head and neck cancer. A second treatment may be co-administered with inducing heat shock response in the cell. The second treatment may comprise an anti-cancer agent.

BRIEF DESCRIPTION OF THE DRAWINGS

FIG. 1 shows that quinacrine (QC) and 9AA prevent HSP70 protein induction in cells treated with proteasome inhibitors.

FIG. 7 shows that the heat sensitivity of tumor cells, but not normal cells, is increased upon treatment with QC and CZ (compound CBL0137).

FIG. 9 shows that quinacrine and 9AA prevent hsp70 synthesis in cells treated with proteasome inhibitors. FIG. 9A shows the results of immunoblotting with anti-hsp70 antibody of protein extracts from HeLa cells treated for 5 h with the proteasome inhibitor MG132 (MG) (5 µM) in combination with the anti-malaria drugs emetine (EM) (1 µM), chloroquine (CQ) (20 µM), quinine (O) (20 µM), or quinacrine (QC) (20 µM). Lane 1 contains extract from untreated HeLa cells. Pirin expression was examined as a protein loading control (L.c.). FIG. 9B shows protein extracts from HeLa cells treated for 5 h with MG132 (5 µM) alone or in combination with 20 µM QC or 9AA as examined by immunoblotting using an antibody specific for hsp70. Negative controls included untreated HeLa cells (lane 1) and cells treated with QC or 9AA in the absence of MG132 (lanes 6 and 7). Pirin was examined as a protein loading control (L.c.). FIG. 9C shows that emetine, but not QC or 9AA, inhibits general protein synthesis. S35-labeled proteins from HeLa cells left untreated (lane 1) or treated for 4 h with QC (20 µM), 9AA (20 µM), or emetine (EM) (1 µM) were analyzed by electrophoresis and autoradiography. FIG. 9D shows that aminoacridines do not affect inhibition of proteasomes by MG132, as indicated by the results of an in vitro proteasome activity assay using extracts of HeLa cells treated for 4 h with the indicated combinations of MG132 (5 µM), QC (20 µM) and 9AA (20 µM). Proteasome activity is shown relative to that in untreated cells (set at 100%). FIG. 9E shows that QC inhibits activation of hsp70A1 transcription by proteasome inhibitors in HeLa cells. 10 µg of total RNA from untreated HeLa cells (lane 1) or treated for 5 h with 0.1 µM Bortezomib (BZ) or 5 µM MG132 (MG) alone or in combination with 20 µM QC were analyzed by Northern blotting with hsp70A1 (top panel) and GAPDH (bottom panel) probes. GAPDH was used to control for the specificity of QC's inhibitory activity and for RNA loading. FIG. 9F shows that aminoacridines do not prevent induction of metallothionein gene expression by $ZnCl_2$. HeLa cells were left untreated (lane 1) or treated for 5 h with 200 μM ZnC12 (Zn) alone or in combination with 20 μM QC or 9AA. 10 μg of total RNA were analyzed by Northern blotting with metallothionein MT1 (MT), hsp70A1, and GAPDH probes.

FIG. 10A shows the results of immunoblotting with anti-hsp70 antibody of protein extracts (10 μg) from HeLa cells treated for 5 h with 5 μM MG132 (MG) or 1 μM 17-DMAG (GM) alone or in combination with 20 μM QC or 9AA. Lane 1 contains extract from untreated HeLa cells. K18 expression was assessed as a protein loading control (L.c). FIG. 10B shows that QC and 9AA suppress transcription of the hsp70A1 gene induced by 17-DMAG or MG132. Northern hybridization of RNA from untreated HeLa cells (lane 1), treated for 5 h with 1 μM 17-DMAG (GM) or 5 μM MG132 (MG) alone, and in combination with 20 μM QC or 9AA. GAPDH mRNA was analyzed to control for inhibitor specificity and RNA loading. FIG. 10C shows that QC and 9AA do not change mRNA accumulation of genes that are not induced by 17-DMAG, as indicated by Northern hybridization of RNA from HeLa cells treated for 5 h with 1 μM 17-DMAG (GM) alone or in combination with 20 μM QC or 9AA. GAPDH, p65RelA, and GRP94 are genes whose expression is not affected by 17-DMAG. Hsp70A1 was included as a positive control for a 17-DMAG inducible gene. FIG. 10D shows that QC suppresses HSF1-dependent expression of an EGFP reporter gene induced by proteotoxic stress. HeLa cells carrying an HSF1-EGFP reporter construct were left untreated, or treated with 0.1 μM of Bortezomib (BZ), 1 μM of 17-DMAG (GM), or 43° C. for 1 h of heat shock (HS) alone or in combination with 20 μM QC. EGFP expression was assessed in 8 h by fluorescent microscopy.

FIG. 11 shows that aminoacridines act downstream of HSF1 activation and translocation to the nucleus. FIG. 11A shows that treatment of HeLa cells with MG132, 17-MAG, or heat shock induces HSF1 DNA binding activity. Electrophoretic mobility shift assays (EMSA) were performed with cytoplasmic extracts from HeLa cells left untreated, treated with 5 μM MG132 (MG) or 1 μM 17-DMAG (GM) for 4 h, or treated with heat shock (43° C.) for 1 h. Complex formation between HSF1 and a $^{32}$P-labeled oligonucleotide probe containing an HSF1 binding site was inhibited by a 50× excess of the same unlabeled oligonucleotide (lane 3), but not by a similar excess of an unlabeled oligonucleotide containing an NFkB binding site (lane 4). The specificity of the detected complex was further confirmed by its super-shift in the presence of anti-HSF1 antibody (lane 7). FIG. 11B shows that QC does not affect nuclear HSF1 DNA binding activity induced by proteotoxic stress. EMSA was performed as in A with a labeled HSF1-specific oligonucleotide probe and nuclear extracts from HeLa cells left untreated (lane 1), or treated for 4 h with 5 μM MG132 (MG) or 1 μM 17-DMAG (GM) alone or in combination with 20 μM QC. FIG. 11C shows that bafilomycin increases the nuclear concentration of QC. HeLa cells were treated with 5 μM QC alone or in combination with 0.5 μM of bafilomycin for 1 h. The intracellular localization of QC was analyzed by UV-microscopy with a blue filter. FIG. 11D shows that bafilomycin increases the HSR inhibitory activity of QC. HeLa cells were left untreated (lane 1) or treated for 5 h with the indicated combinations of 5 μM MG132 (MG), 0.5 μM bafilomycin (Baf), and variable amounts of QC. Whole cell protein extracts were analyzed by Western blotting with anti-hsp70 antibody. Pirin was examined as a protein loading control (L.c.).

FIG. 12 shows that QC enhances the cytotoxicity of proteotoxic stress inducers. FIG. 12A shows the toxicity of drug combinations as measured using a cell viability assay. HeLa cells were treated for 4 h with the indicated combinations of 17-DMAG (1 μM) and QC (10 or 20 μM). Cell viability was assessed 72 h later by methylene blue staining. The data shown are the average of three experiments. FIG. 12B shows the toxicity of bortezomib/QC treatment as assessed using a cell viability assay as in FIG. 12A. HeLa cells were treated for 4 h with 0.1 μM bortezomib (BZ) alone or in combination with 10 μM QC. The data shown are the average of 2 experiments. FIG. 12C shows immunoblotting analysis of apoptosis in HeLa cells treated with combinations of bortezomib (BZ) (0.1 μM), 17-DMAG (GM) (1 μM), and QC (10 μM). Full-length PARP and K18 proteins as well as apoptosis-specific proteolytic fragments (PARP/apopt and K18/apopt) are indicated. FIG. 12D shows that siRNA-mediated knockdown of Hsp70 sensitizes cells to bortezomib and 17-DMAG, as indicated by immunoblotting of proteins from hsp70 siRNA (siRNA)-expressing HeLa cells treated with the indicated concentrations of 0.1 μM bortezomib (BZ), 20 μM of QC, and 1 μM 17-DMAG (GM). Protein extracts were prepared from cells transfected with hsp70 siRNA for 24 h and treated with bortezomib and DMAG overnight. Expression of hsp70 and apoptosis-specific cleavage of K18 was assessed with the corresponding antibodies. Control HeLa cells were untreated with drugs (lane1), or treated overnight with amount of drugs indicated above (lanes 5-9). FIG. 12E shows that the caspase inhibitor ZVAD-FMK protects cells from apoptosis induced by combinations of proteotoxic stress and aminoacridines, as indicated by immunoblotting analysis of hsp70 protein levels and apoptosis-specific cleavage of K18 in HeLa cells treated overnight with the indicated combinations of 1 μM 17-DMAG (GM), 0.1 μM bortezomib (BZ), 20 μM QC, and 20 μM ZVAD-FMK (ZVAD). Treatment of cells with anti-Fas antibody (Fas, lane 9) and the combination of anti-Fas antibody and ZVAD-FMK (lane 10) provided positive controls for induction of apoptosis and the protective effect of ZVAD-FMK, respectively.

FIG. 13A shows that QC suppresses hsp70 synthesis in response to proteotoxic stress in MCA205 and B-16 cells. RNA from control cells and cells treated for 5 h with 1 μM 17-DMAG (GM) in the presence or absence of 20 μM QC was analyzed by Northern hybridization with hsp70A1 and GAPDH probes. FIG. 13B shows the results of cell viability assays of MCA205 and B-16 cells treated for 4 h with 1 μM 17-DMAG (GM) in combination with 20 μM QC. Cells were harvested, diluted 1:50 and assayed for cell viability by methylene blue staining 72 h later. The data shown are the average of two experiments. FIG. 13C shows that intra-tumor injection of QC blocks 17-DMAG-induced hsp70 expression. C57BL/6 mice carrying MCA205 tumors were given a single intra-tumor injection of PBS (control), 25 μg 17-DMAG (GM), or 1.25 mg QC+25 μg 17-DMAG. Five hours later, mice were sacrificed. RNA prepared from the tumors was analyzed by Northern hybridization with a hsp70A1 specific probe. Hybridization with a GAPDH probe was used as an RNA loading control (L.c.). The data shown is from a single tumor for each treatment. These are representative data of two experiments. FIGS. 13D and E show the results of injecting C57BL/6 mice with MCA205 (D) or B-16 (E) cells. Average tumor volume within each group is shown.

DETAILED DESCRIPTION

Figure 2:
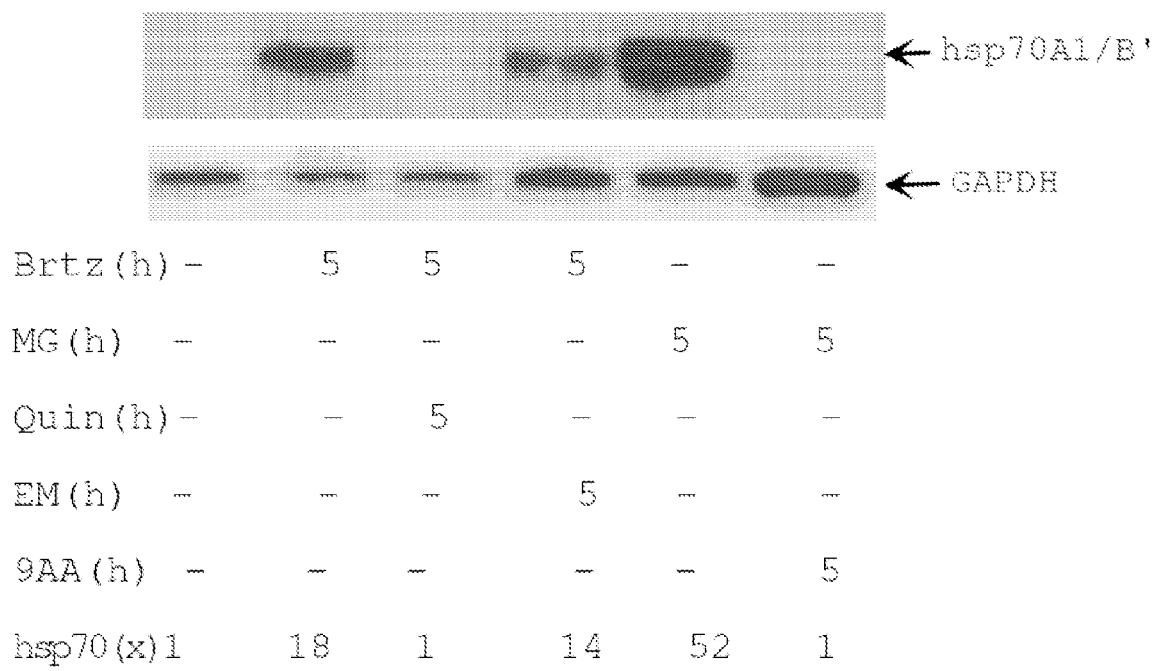
FIG. 2 shows that QC and 9AA inhibit transcription of HSP70 gene in response to proteasome inhibitors.

The inventors have made the surprising discovery that inducing heat shock response in combination with inhibiting adaptive heat shock response can induce cell death. While not bound by theory, inhibitors of adaptive heat shock response may prevent the ability of a cell to tolerate the induction of heat shock response by suppressing HSF-1, the major mediator of inducible heat shock-triggered transcription. Heat shock proteins are chaperone proteins that prevent the otherwise fatal consequences of damaging stimuli by disaggregating, refolding, and renaturing misfolded proteins. The protective effect of heat shock proteins may also lie in their ability to suppress several forms of cell death, including apoptosis. In the absence of heat shock proteins, cells are less able to respond to chemical, environmental, and physiological stresses. In particular, tumor cells may be more sensitive to inhibition of the heat shock response, since they typically express higher levels of heat shock proteins and may rely on these elevated levels as a mechanism for suppressing the effects of cumulative mutations that would otherwise result in expression of deleterious proteins. Accordingly, the combination of inhibiting adaptive heat shock response and inducing heat shock response provides a simple and flexible approach to inducing cell death.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

a. Acryl

The term "acryl" as used herein alone or in combination may refer to a group represented by CH2=C(O)C(O)O— where Q is an aliphatic or aromatic group.

b. Acyl

The term "acylamino" may mean R(=O)N—, wherein R is alkyl or aryl.

c. Administer

As used herein, the terms "administer" when used to describe the dosage of a compound, may mean a single dose or multiple doses of the compound.

d. Aliphatic

The term "aliphatic" as used herein may refer to an unbranched, branched or cyclic hydrocarbon group, which may be substituted or unsubstituted, and which may be saturated or unsaturated, but which is not aromatic. The term aliphatic may further include aliphatic groups, which comprise oxygen, nitrogen, sulfur or phosphorous atoms replacing one or more carbons of the hydrocarbon backbone.

e. Alkoxy

The term "alkoxy" as used herein alone or in combination may refer to an alkyl, alkenyl or alkynyl group bound through a single terminal ether linkage. Examples of alkoxy groups may include methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy. Alkoxy may also mean—OR, wherein R is alky.

f. Alkoxyalkyl

The term "alkoxyalkyl" means an alkyl group wherein a hydrogen has been replaced by an alkoxy group.

g. Alkenyl

The term "alkenyl" as used herein alone or in combination may refer to a branched or unbranched, unsaturated aliphatic group containing at least one carbon-carbon double bond which may occur at any stable point along the chain. Representative examples of alkenyl groups may include ethenyl, E and Z pentenyl, decenyl and the like.

h. Alkyl

The term "alkyl" as used herein alone or in combination may refer to chained or branched hydrocarbon groups containing the indicated number of carbon atoms, typically methyl, ethyl, and straight chain and branched propyl and butyl groups. The term "cycloalkyl" is defined as a cyclic hydrocarbon group containing the indicated number of carbon atoms, e.g., cyclopropyl, cyclobutyl, cyclohexyl, and cyclopentyl.

i. Alkylthio

The term "alkylthio" may mean —SR, wherein R is alkyl j. Alkynyl

The term "alkynyl" as used herein alone or in combination may refer to a branched or unbranched, unsaturated aliphatic group containing at least one carbon-carbon triple bond which may occur at any stable point along the chain. Representative examples of alkynyl groups may include ethynyl, propynyl, propargyl, butynyl, hexynyl, decynyl and the like.

k. Amino

The term "amino" as used herein alone or in combination may refer to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like. Amino may also mean means —NH$_2$, and the term "alkylamino" may mean —NR$_2$, wherein at least one R is alkyl and the second R is alkyl or hydrogen.

l. Aromatic

The term "aromatic" as used herein may refer to an unsaturated cyclic hydrocarbon group having 4n+2 delocalized p(pi) electrons, which may be substituted or unsubstituted. The term aromatic may further include aromatic groups, which comprise a nitrogen atom replacing one or more carbons of the hydrocarbon backbone. Examples of aromatic groups may include phenyl, naphthyl, thienyl, furanyl, pyridinyl, (is)oxazoyl and the like.

m. Alkylsulfinyl

The term "alkylsulfinyl" means R—SO$_2$—, wherein R is alkyl.

n. Alkylsulfonyl

The term "alkylsulfonyl" means R—SO$_3$—, wherein R is alkyl.

o. Morpholino Moiety

The term "morpholino moiety" means

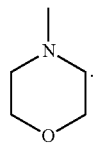

p. Tetrahydrofuryl Moiety

The term "tetrahydrofuryl moiety" means

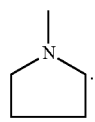

q. Piperidinyl Moiety

The term "piperidinyl moiety" means

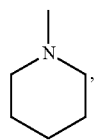

optionally substituted with an —OH or —CH$_2$OH group.

r. Aryl

The term "aryl" as used herein alone or in combination may refer to a substituted or unsubstituted aromatic group, which may be optionally fused to other aromatic or non-aromatic cyclic groups. Representative examples of aryl groups may include phenyl, benzyl, naphthyl, benzylidine, xylyl, styrene, styryl, phenethyl, phenylene, benzenetriyl and the like.

s. Aryloxy

The term "aryloxy" as used herein alone or in combination may refer to an aryl group bound through a single terminal ether linkage.

t. Branched

The term "branched" as used herein may refer to a group containing from 1 to 24 backbone atoms wherein the backbone chain of the group contains one or more subordinate branches from the main chain. A branched group may contain from 1 to 12 backbone atoms. Examples of branched groups may include isobutyl, t-butyl, isopropyl, CH$_2$CH$_2$CH(CH$_3$)CH$_2$CH$_3$, CH$_2$CH(CH$_2$CH$_3$)CH$_2$CH$_3$, CH$_2$CH$_2$C(CH$_3$)$_2$CH$_3$, CH$_2$CH$_2$C(CH$_3$)$_3$ and the like.

u. Cancer

As used herein, the term "cancer" may mean any condition characterized by resistance to apoptotic stimuli.

v. Cancer Treatment

As used herein, the term "cancer treatment" may mean any treatment for cancer known in the art including chemotherapy and radiation therapy.

w. Carbonyl

The term "carbonyl" or "carboxy" as used herein alone or in combination may refer to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

x. Combination

As used herein, the term "combination with" or "co-administered" when used to describe administration of an aminoacridine and an additional treatment may mean that the aminoacridine may be administered prior to, together with, or after the additional treatment, or a combination thereof.

y. Cyano

The term "cyano," "cyanate," or "cyanide" as used herein alone or in combination may refer to a carbon-nitrogen double bond. Representative examples of cyano groups include, but are not limited to, isocyanate, isothiocyanate and the like. The term "cyano" means —CN.

z. Cyclic

The term "cyclic" or "cyclo" as used herein alone or in combination may refer to a group having one or more closed rings, whether unsaturated or saturated, possessing rings of from 3 to 12 backbone atoms, or 3 to 7 backbone atoms.

aa. Effective Amount

The term "effective amount," when used in reference to a compound, product, or composition as provided herein, may mean a sufficient amount of the compound, product or composition to provide the desired result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

bb. Haloalkyl

The term "haloalkyl" means an alkyl group substituted with one or more, e.g., 1 to 3, halo substituents, either fluoro, chloro, bromo, iodo, or combinations thereof. Similarly, "halocycloalkyl" is defined as a cycloalkyl group having one or more halo substituents.

The term "aryl," alone or in combination, means a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2 chlorophenyl, 3-chlorophenyl, 4-chlorophenyl, 2-methylphenyl, 4-methoxyphenyl, 3 trifluoromethylphenyl, 4-nitrophenyl, and the like.

cc. Halogen

The term "halogen," "halide" or "halo" as used herein alone or in combination may refer to fluorine "F", chlorine "Cl", bromine "Br", iodine "I", and astatine "At". Representative examples of halo groups may include chloroacetamido, bromoacetamido, idoacetamido and the like.

dd. Hetero

The term "hetero" as used herein combination may refer to a group that includes one or more atoms of any element other than carbon or hydrogen. Representative examples of hetero groups may include those groups that contain heteroatoms including nitrogen, oxygen, sulfur and phosphorus.

ee. Heteroaryl

The term "heteroaryl" means a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazonyl, and thiadiazolyl.

The term "alkylene" means an alkyl group having a substituent. For example, the term "C1-3alkylenearyl" refers to an alkyl group containing one to three carbon atoms and substituted with an aryl group.

ff. Heterocycle

The term "heterocycle" as used herein may refer to a cyclic group containing a heteroatom. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

gg. Heterocyloalkyl

The term "heterocycloalkyl" means monocyclic, bicyclic, and, tricyclic cycloalkyl groups containing one or more heteroatoms selected from the group consisting of oxygen, nitrogen, and sulfur in the ring structure. A "heterocyclocalkyl" group also can contain an oxo group (=O) attached to the ring. Nonlimiting examples of heterocycloalkyl groups include, but are not limited to, 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

hh. Hydroxy

The term "hydroxy" means —OH.

ii. Hydroxyalkyl

The term "hydroxyalkyl" means an alkyl group wherein a hydrogen has replaced by a hydroxy group.

jj. Lower

The term "lower" as used herein may refer to a group with 1 to 6 backbone atoms.

kk. Nitro

The term "nitro" means —NO$_2$.

ll. Optional

The term "optional" or "optionally" as used herein may mean that the subsequently described event or circumstance may or may not occur, and that the description includes instances where said event or circumstance occurs and instances where it does not. For example, the phrase "optionally substituted alkyl" may mean that the alkyl group may or may not be substituted and that the description includes both unsubstituted alkyl and alkyl where there is a substitution.

mm. Peptide

A "peptide" or "polypeptide" is a linked sequence of amino acids and may be natural, synthetic, or a modification or combination of natural and synthetic.

nn. Phosphate-Containing Group

The term "phosphate-containing group" as used herein may refer to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

oo. Saturated

The term "saturated" as used herein may refer to a group where all available valence bonds of the backbone atoms are attached to other atoms. Representative examples of saturated groups may include butyl, cyclohexyl, piperidine and the like.

pp. Substituted

The term "substituted" as used herein may refer to a group having one or more hydrogens or other atoms removed from a carbon or suitable heteroatom and replaced with a further group. Substituted groups may be substituted with one to five, or one to three substituents. An atom with two substituents is denoted with "di," whereas an atom with more than two substituents is denoted by "poly." Representative examples of such substituents may include aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

qq. Sulfur-Containing Group

The term "sulfur-containing group" as used herein may refer to a group containing a sulfur atom. Representative examples include, but are not limited to, sulfhydryls, sulfenos, sulfinos, sulfinyls, sulfos, sulfonyls, thios, thioxos and the like.

rr. Treat

"As used herein, the term "treat" or "treating" when referring to protection of a mammal from a condition, may mean preventing, suppressing, repressing, or eliminating the condition. Preventing the condition involves treating the mammal prior to onset of the condition. Suppressing the condition involves treating the mammal after induction of the condition but before its clinical appearance. Repressing the condition involves treating the mammal after clinical appearance of the condition such that the condition is reduced or maintained. Elimination the condition involves treating the mammal after clinical appearance of the condition such that the mammal no longer suffers the condition.

ss. Trifluoromethoxy

The term "trifluoromethoxy" means —OCF$_3$.

tt. Trifluoromethyl

The term "trifluoromethyl" means —CF$_3$.

uu. Tumor Cell

As used herein, the term "tumor cell" may mean any cell characterized by resistance to apoptotic stimuli.

vv. Unbranched

The term "unbranched" as used herein may refer to a group containing from 1 to 24 backbone atoms wherein the backbone chain of the group extends in a direct line. An unbranched group may contain from 1 to 12 backbone atoms.

ww. Unsaturated

The term "unsaturated" as used herein may refer to a group where at least one available valence bond of two adjacent backbone atoms is not attached to other atoms. Representative examples of unsaturated groups may include —$CH_2CH_2CH$=$CH_2$, phenyl, pyrrole and the like.

xx. Unsubstituted

The term "unsubstituted" as used herein may refer to a group that does not have any further groups attached thereto or substituted therefor.

2. METHOD FOR INDUCING CELL DEATH

Provided herein is a method for inducing cell death. Cell death may be induced by inhibiting adaptive heat shock response in combination with inducing heat shock response in a cell. The heat shock response may be induced by administering a heat-shock response-inducing agent to the cell, or by increasing the internal temperature of the cell with a heating means.

a. Inhibiting Adaptive Heat Shock Response

The inhibitor of adaptive heat shock response may be an agent capable of acting as a DNA-intercalating, non-genotoxic agent that can suppress HSF-1-mediated transcription. The inhibitor of adaptive heat shock response may be aminoacridine, carbazole, or a derivative thereof.

(1) Aminoacridine

The aminoacridine may have the following formula:

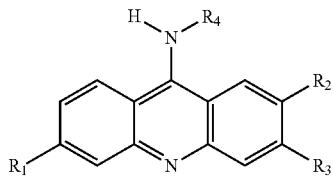

(Compound 1)

wherein, $R_1$ is H or halogen;

$R_2$ is H or optionally substituted alkoxy;

$R_3$ is H or optionally substituted alkoxy; and $R_4$ is H or optionally substituted aliphatic, aryl, or heterocycle.

The aminoacridine may be 9-aminoacridine or Mepacrine, which is otherwise known as Quinacrine. The aminoacridine may also be as described in Intl. Pat. Pub. No. WO/06/12419, the contents of which are incorporated herein by reference.

(2) Carbazole Derivative

The inhibitor of adaptive heat shock response may be a carbazole or derivative thereof. The inhibitor of adaptive heat shock response may be a carbazole or derivative thereof. The carbozole or derivative thereof may be as described in U.S. Provisional Application No. 61/102,913, filed Oct. 6, 2008, the contents of which are incorporated herein by reference.

The carbozole or derivative thereof may be of the formula (I):

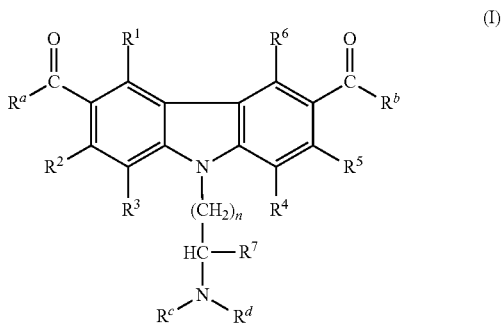

wherein $R^a$ is selected from the group consisting of hydrogen, $C_{1-6}$alkyl, $C_{1-6}$haloalkyl, cycloalkyl, heterocycloalkyl, aryl, heteroaryl, $OR^e$, $N(R^e)_2$, and $SR^e$, or either $R^a$ and $R^1$ or $NR^e$ and $R^1$ together with the carbon atoms to which they are attached form a five or six-membered aliphatic carbocyclic or heterocyclic ring;

$R^b$ is selected from the group consisting of hydrogen, $C_{1-6}$alkyl, $C_{1-6}$haloalkyl, cycloalkyl, heterocycloalkyl, aryl, heteroaryl, $OR^e$, $N(R^e)_2$, and $SR^e$, or either $R^b$ and $R^6$ or $NR^e$ and $R^6$ together with the carbon atoms to which they are attached form a five or six-membered aliphatic carbocyclic ring or a five or six-membered aliphatic carbocyclic or heterocyclic ring;

$R^c$ is selected from the group consisting of hydrogen, $C_{1-6}$alkyl, $C_{1-6}$hydroxyalkyl, cycloalkyl, heterocycloalkyl, aryl, heteroaryl, and $C(=O)R^e$, or $R^c$ and $R^d$ are taken together to form a five, six, or seven-membered aliphatic ring, optionally containing an oxygen atom;

$R^d$ is selected from the group consisting of hydrogen, $C_{1-6}$ alkyl, cycloalkyl, heterocycloalkyl, aryl, heteroaryl, and $C(=O)R^e$, or $R^d$ and $R^7$ together with the atoms to which they are attached form a five or six-membered aliphatic ring;

$R^e$, independently, is selected from the group consisting of hydrogen, $C_{1-6}$ alkyl, cycloalkyl, heterocycloalkyl, aryl, and heteroaryl, or two $R^e$ groups taken together with a nitrogen to which they are attached to form a five or six-membered aliphatic ring;

$R^1$, $R^2$, $R^3$, $R^4$, $R^5$, and $R^6$, independently, are selected from the group consisting of hydrogen, $C_{1-6}$ alkyl, cycloalkyl, heterocycloalkyl, aryl, heteroaryl, halo, $OR^e$, $C(=O)R^e$, $C(=O)OR^e$, $OC(=O)R^e$, $C(=O)N(R^e)_2$, $C(=O)NR^eSO_2R^e$, $N(R^e)_2$, $NR^eC(=O)R^e$, $NR^eC(=O)N(R^e)_2$, CN, $NO_2$, $CF_3$, $OCF_3$, $SR^e$, $SOR^B$, $SO_2R^e$, $SO_2N(R^e)_2$, and $OSO_2CF_3$;

$R^7$ is selected from the group consisting of hydrogen, $C_{1-6}$ alkyl, cycloalkyl, heterocycloalkyl, aryl, and heteroaryl; and n is 0, 1, 2, 3, 4, or 5, or a pharmaceutically acceptable salt or hydrate thereof.

The carbozole or derivative thereof may have a general structural formula (Ia.):

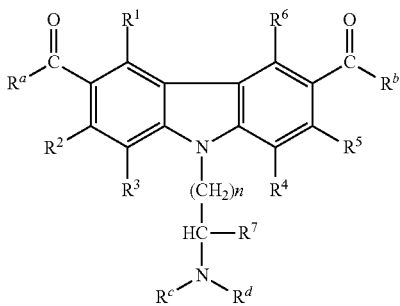

(Ia)

wherein $R^a$ is $C_{1-3}$ alkyl, $C_{1-4}$ haloalkyl, $C_{3-5}$ cycloalkyl, $N(R^e)_2$, or $OR^e$, or $R^a$ and $R^1$ together with the carbon atoms to which they are attached form a five or six-membered aliphatic carbocyclic ring;
$R^b$ is $C_{1-4}$ alkyl, $C_{1-4}$ haloalkyl, $C_{3-5}$ cycloalkyl, $N(R^e)_2$, or $OR^e$, or $R^b$ and $R^6$ together with the carbon atoms to which they are attached form a five or six-membered aliphatic carbocyclic ring or a five or six-membered aliphatic ring containing one nitrogen atom;
$R^c$ is $C_{1-6}$ alkyl, $C_{3-5}$ cycloalkyl, or $C_{1-3}$ hydroxyalkyl;
$R^d$ is hydrogen, $C_{1-4}$ alkyl, or $C_{3-5}$ cycloalkyl, or $R^d$ and $R^7$ together with the atoms to which they are attached form a five or six-membered aliphatic ring containing one nitrogen atom or $R^c$ and
$R^d$ are taken together to form a six or seven-membered aliphatic ring, optionally containing an oxygen atom;
$R^e$, independently, is hydrogen or $C_{1-3}$ alkyl;
$R^1$ is hydrogen or $C_{1-3}$ alkyl;
$R^2$ is hydrogen, hydroxy, or $C_{1-3}$ alkoxy;
$R^3$ and $R^4$, independently, are hydrogen or $C_{1-3}$ alkyl;
$R^5$ is hydrogen, hydroxy, $C_{1-3}$alkoxy, or halo;
$R^6$ is hydrogen, $C_{1-3}$alkyl, $C_{1-3}$alkoxy, or halo;
$R^7$ is hydrogen or $C_{1-3}$ alkyl; and
n is 0, 1, 2, 3, 4, or 5,
or a pharmaceutically acceptable salt or hydrate thereof.

The carbozole or derivative thereof may have a general structural formula (Ib):

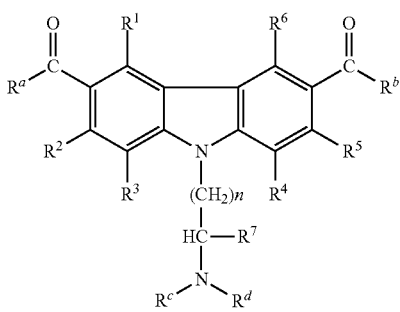

(Ib)

wherein $R^a$ is methyl, ethyl, n-propyl, cyclopropyl, $NH(CH_3)$, or $OCH_3$, or $R^a$ and $R^1$ together with the carbon atoms to which they are attached form a five-membered aliphatic carbocyclic ring;
$R^b$ is methyl, ethyl, n-propyl, cyclopropyl, $NH(CH_3)$, or $OCH_3$, or $R^b$ and $R^6$ together with the carbon atoms to which they are attached form a five-membered aliphatic carbocyclic ring or a five-membered aliphatic ring containing one nitrogen atom;

$R^c$ is methyl, ethyl, n-propyl, isopropyl, cyclobutyl, or 2-hydroxyethyl;
$R^d$ is hydrogen, methyl, ethyl, or cyclobutyl, or $R^d$ and $R^7$ together with the atoms to which they are attached form a five-membered aliphatic ring containing one nitrogen atom, or $R^c$ and $R^d$ are taken together to form a morpholino moiety, a tetrahydrofuryl
moiety, a piperidinyl moiety, or a

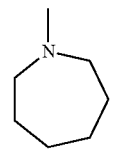

moiety, a

moiety;
$R^1$ is hydrogen;
$R^2$ is hydrogen, hydroxy, or methoxy;
$R^3$ and $R^4$ are hydrogen;
$R^5$ is hydrogen, hydroxy, methoxy, or fluoro;
$R^6$ is hydrogen, methyl, methoxy, or fluoro;
$R^7$ is hydrogen; and
n is 1 or 2,
or a pharmaceutically acceptable salt or hydrate thereof.

The carbozole or derivative thereof may have a structural formula (II):

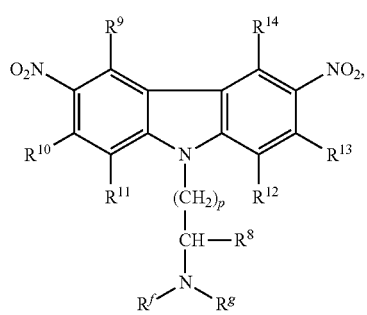

(II)

wherein $R^f$ is selected from the group consisting of hydrogen, $C_{1-6}$ alkyl, cycloalkyl, heterocycloalkyl, aryl, heteroaryl, and $C(=O)R^h$, or $R^f$ and $R^g$ are taken together to form a five, six, or seven-membered aliphatic ring optionally containing an oxygen atom;
$R^g$ is selected from the group consisting of hydrogen, $C_{1-6}$ alkyl, cycloalkyl, heterocycloalkyl, aryl, heteroaryl, and $C(=O)R^h$, or $R^g$ and $R^h$ together with the atoms to which they are attached form a five, six, or seven-membered aliphatic ring;
$R^h$, independently, is selected from the group consisting of hydrogen, $C_{1-6}$ alkyl, cycloalkyl, heterocycloalkyl, aryl, and heteroaryl, or two $R^h$ groups taken together with a nitrogen to which they are attached to form a five or six-membered aliphatic ring;

$R^9$, $R^{10}$, $R^{11}$, $R^{12}$, $R^{13}$, and $R^{14}$, independently, are selected from the group consisting of hydrogen, $C_{1-6}$ alkyl, cycloalkyl, heterocycloalkyl, aryl, heteroaryl, halo, $OR^h$, $C(=O)R^h$, $C(=O)OR^h$, $OC(=O)R^h$, $C(=O)N(R^h)_2$, $C(=O)NR^hSO_2R^h$, $N(R^h)_2$, $NR^hC(=O)R^h$, $NR^hC(=O)N(R^h)_2$, CN, $NO_2$, $CF_3$, $OCF_3$, $SR^h$, $SOR^h$, $SO_2R^h$, $SO_2N(R^h)_2$, and $OSO_2CF_3$;

$R^8$ is selected from the group consisting of hydrogen, $C_{1-6}$ alkyl, cycloalkyl, heterocycloalkyl, aryl, and heteroaryl; and p is 0, 1, 2, 3, 4, or 5, with the proviso that when p is 2, one of $R^f$ and $R^g$ is different from ethyl, or a pharmaceutically acceptable salt or hydrate thereof.

The carbozole or derivative thereof may have a general structural formula (IIa):

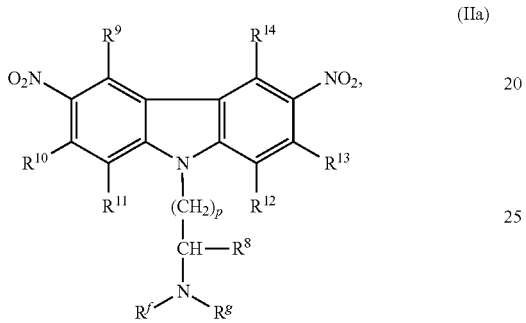

(IIa)

wherein $R^f$ is $C_{1-6}$ alkyl;

$R^g$ is hydrogen or $C_{1-4}$ alkyl, or $R^g$ and $R^8$ together with the atoms to which they are attached form a five or six-membered aliphatic ring containing one nitrogen atom;

$R^9$ is hydrogen or $C_{1-3}$ alkyl;

$R^{10}$ is hydrogen, hydroxy, or $C_{1-3}$ alkoxy;

$R^{11}$ and $R^{12}$, independently, are hydrogen or $C_{1-3}$ alkyl;

$R^{13}$ is hydrogen, hydroxy, $C_{1-3}$ alkoxy, or halo;

$R^{14}$ is hydrogen, $C_{1-3}$ alkyl, or $C_{1-3}$ alkoxy;

$R^8$ is hydrogen or $C_{1-3}$ alkyl; and p is 0, 1, 2, 3, 4, or 5, with the proviso that when p is 2, one of $R^f$ and $R^g$ is different from ethyl, or a pharmaceutically acceptable salt or hydrate thereof.

The carbozole or derivative thereof may have a structural formula (IIb):

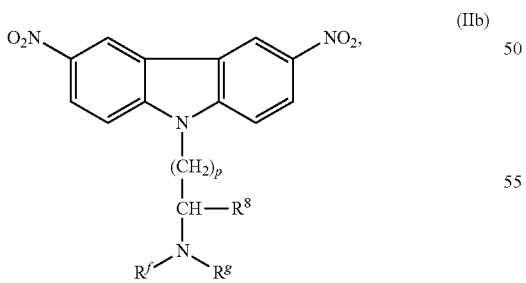

(IIb)

wherein $R^f$ is methyl or ethyl;

$R^g$ is hydrogen or methyl, or $R^g$ and $R^8$ together with the atoms to which they are attached form a five-membered aliphatic ring containing one nitrogen atom;

$R^8$ is hydrogen; and p is 1 or 2, or a pharmaceutically acceptable salt or hydrate thereof.

The carbozole or derivative thereof may have a formula selected from the group consisting of:

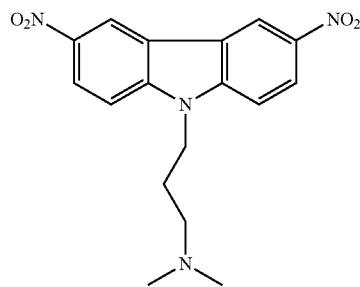

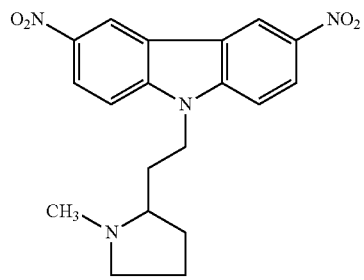

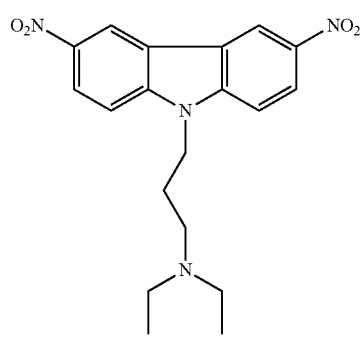

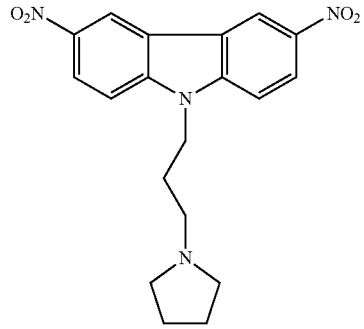

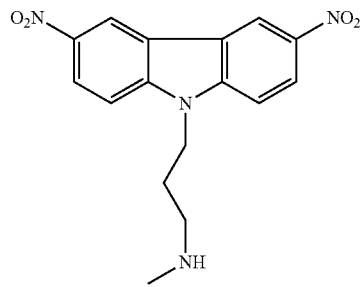

17
-continued
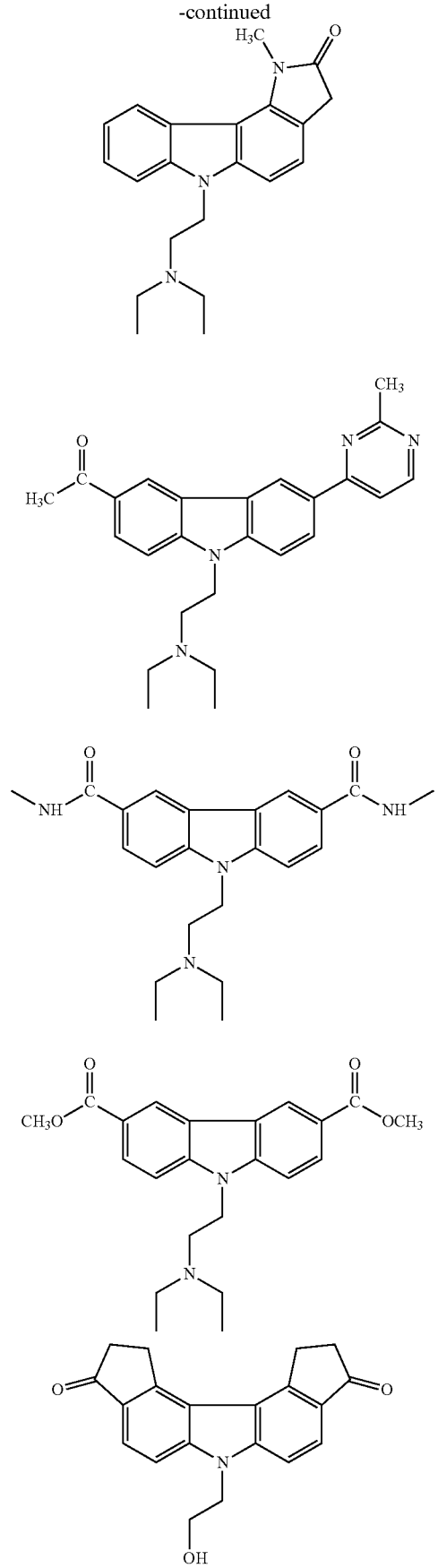
18
-continued
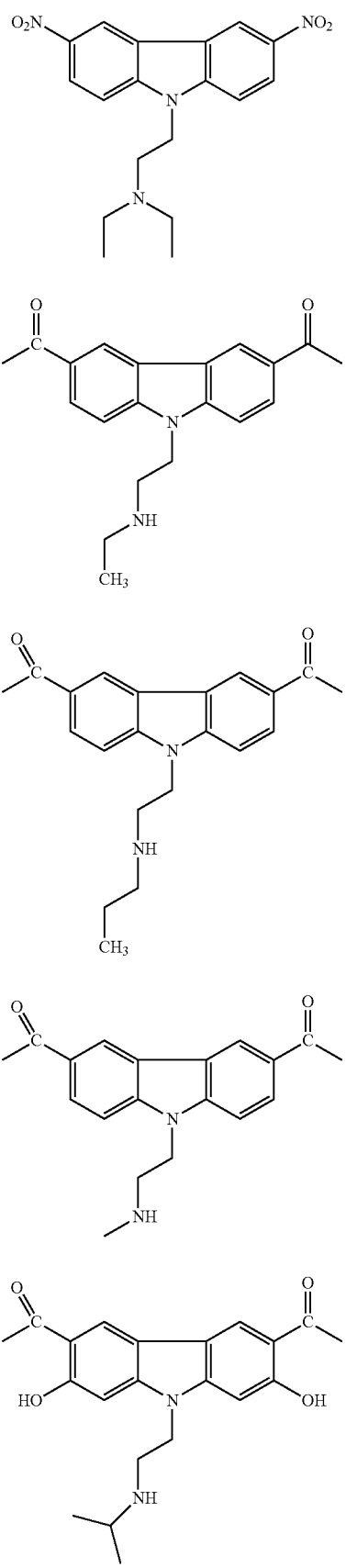

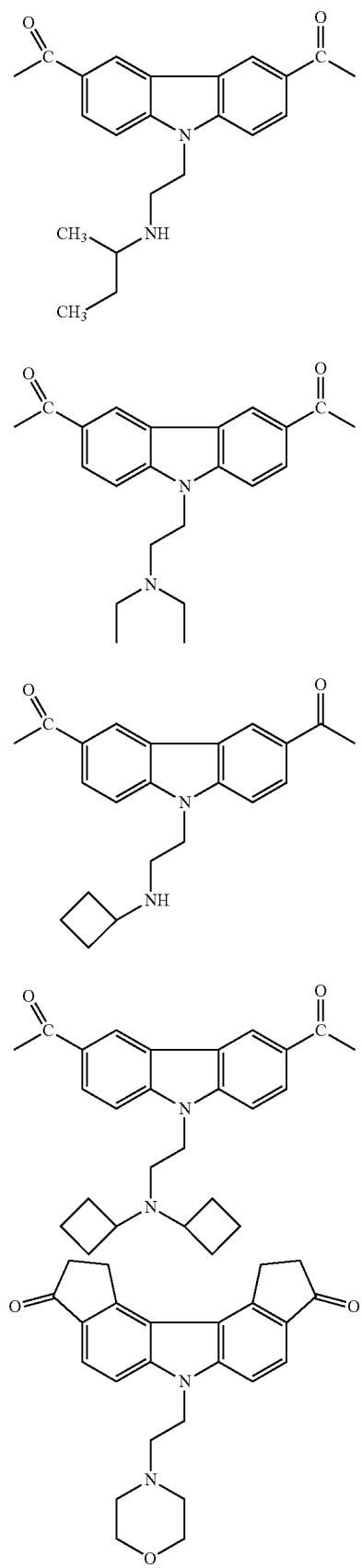
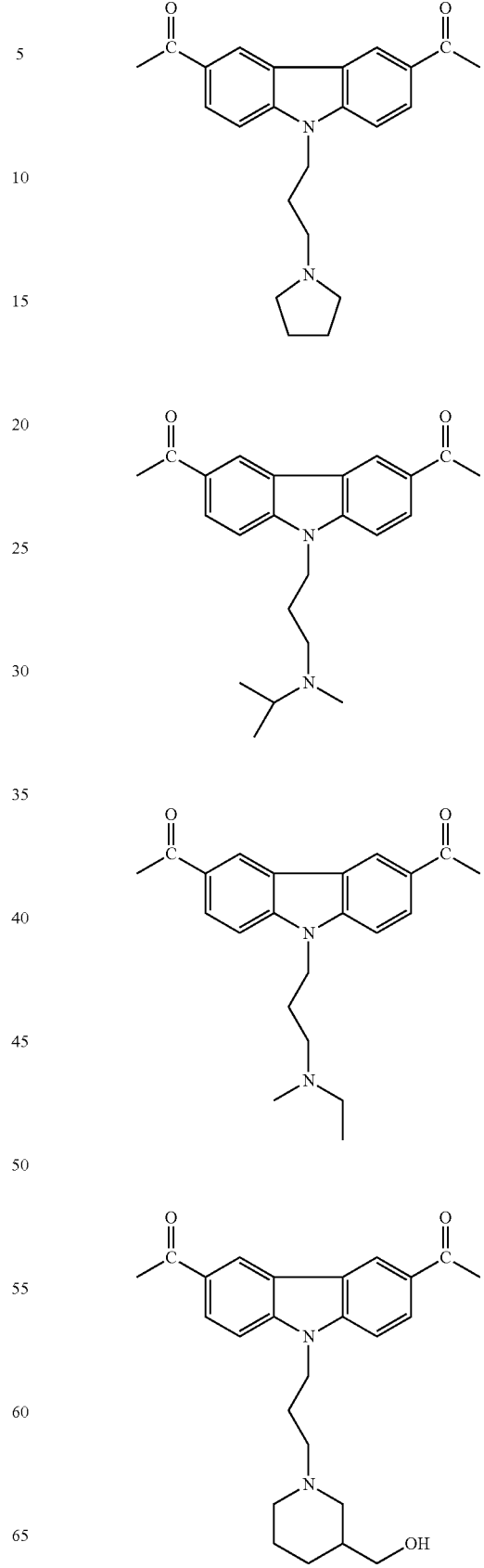

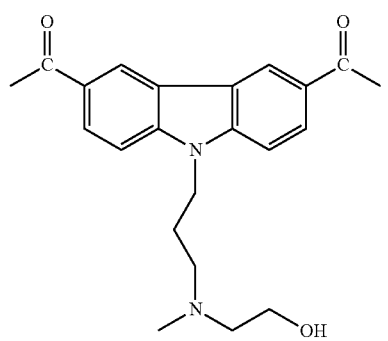
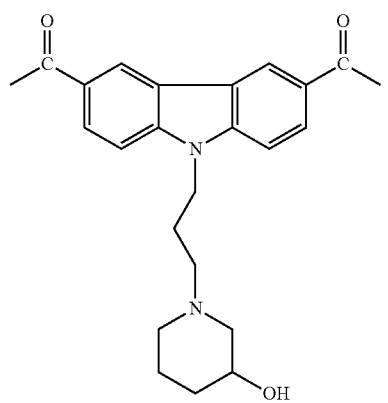
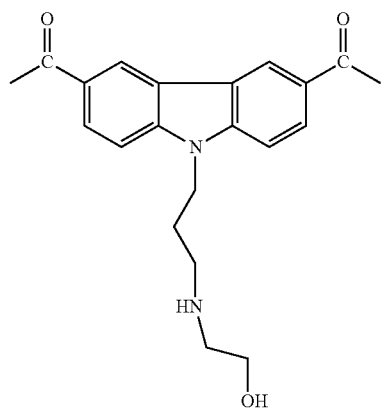
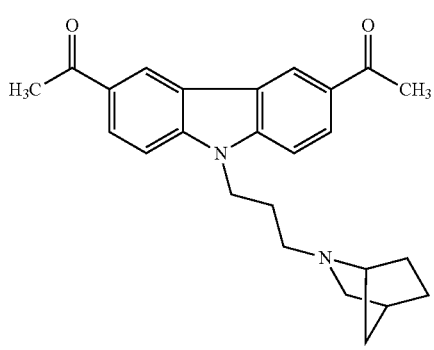
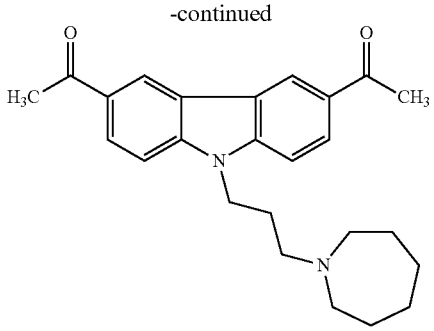
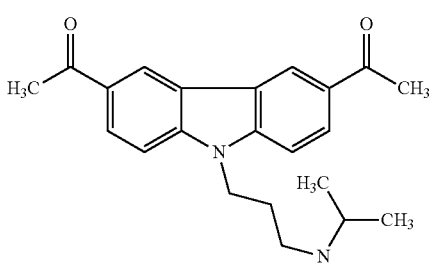
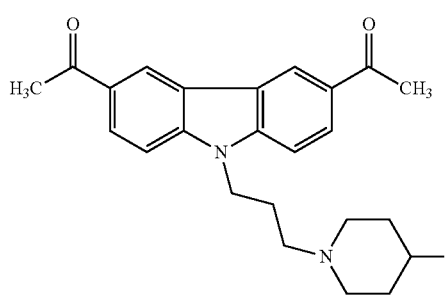
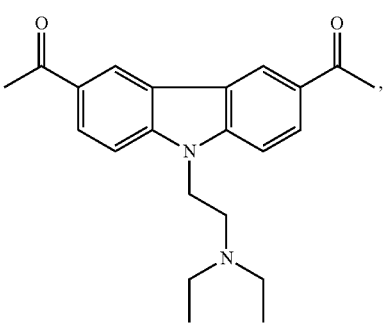
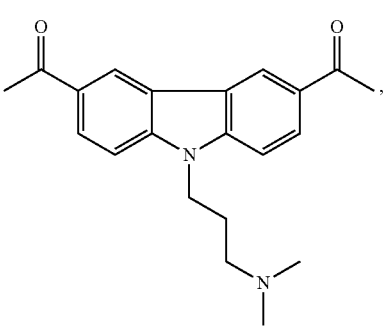

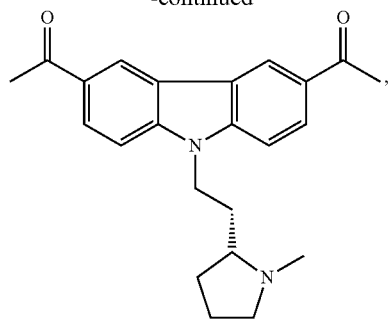
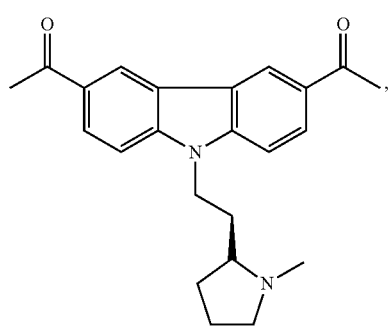
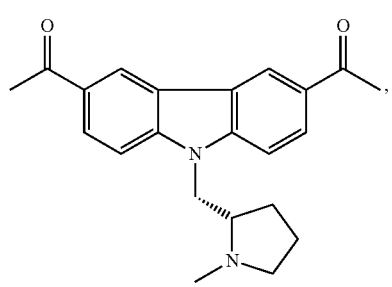
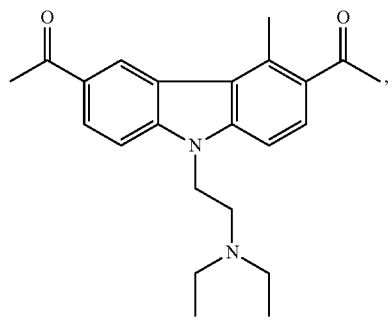
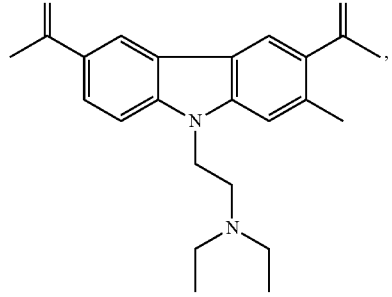
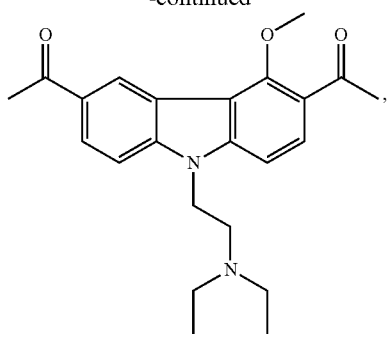
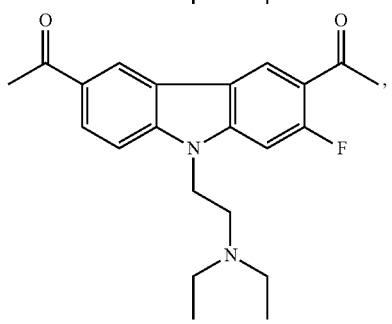
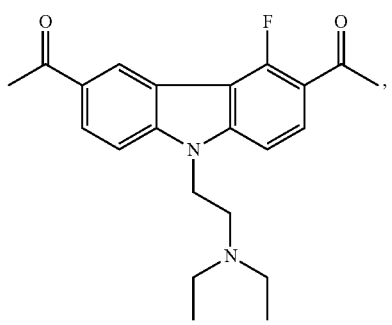
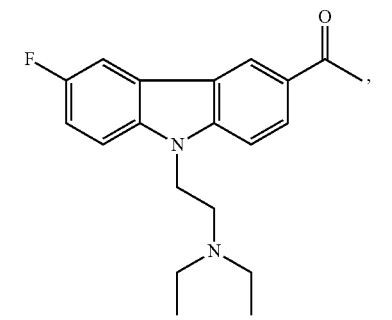
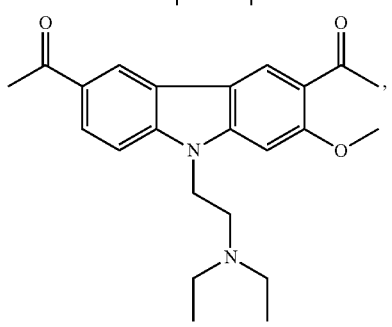

25
-continued
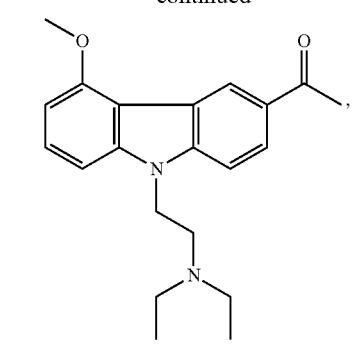
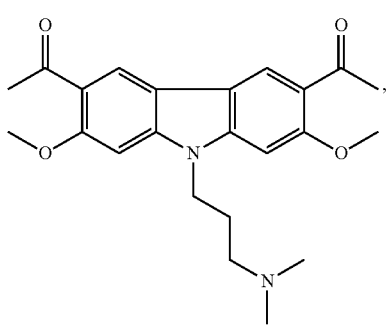
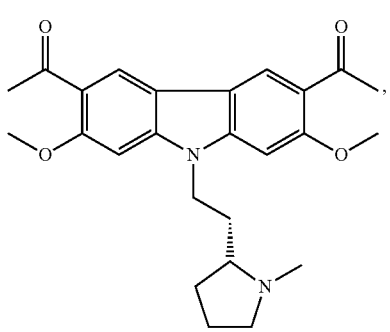
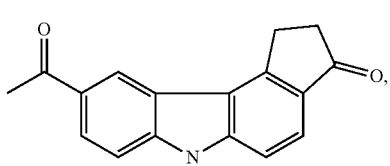
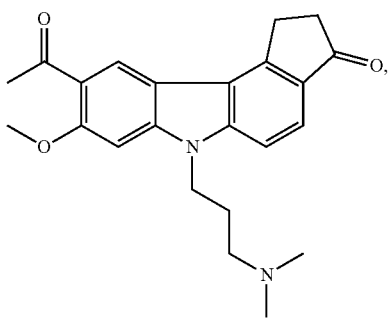
26
-continued
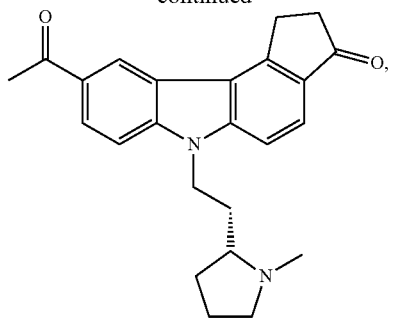
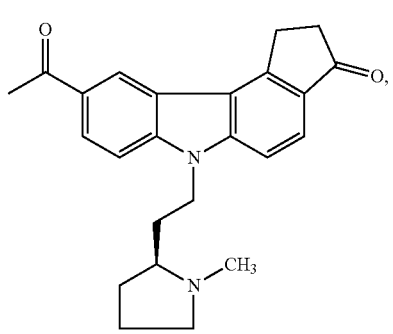
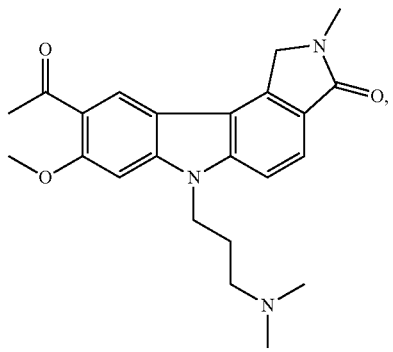
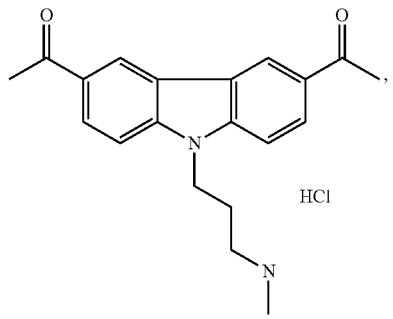
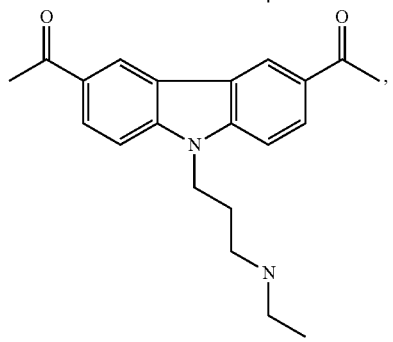

27
-continued
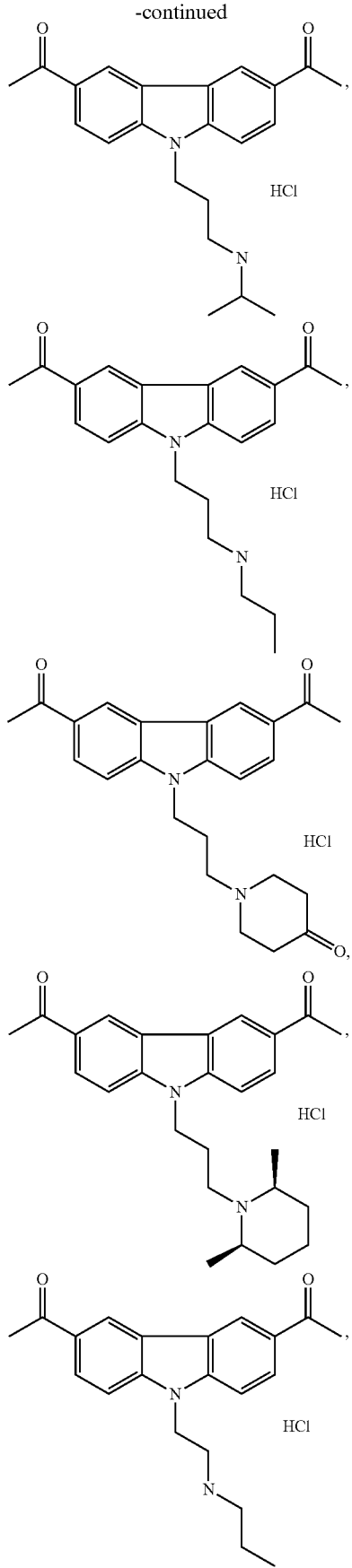
28
-continued
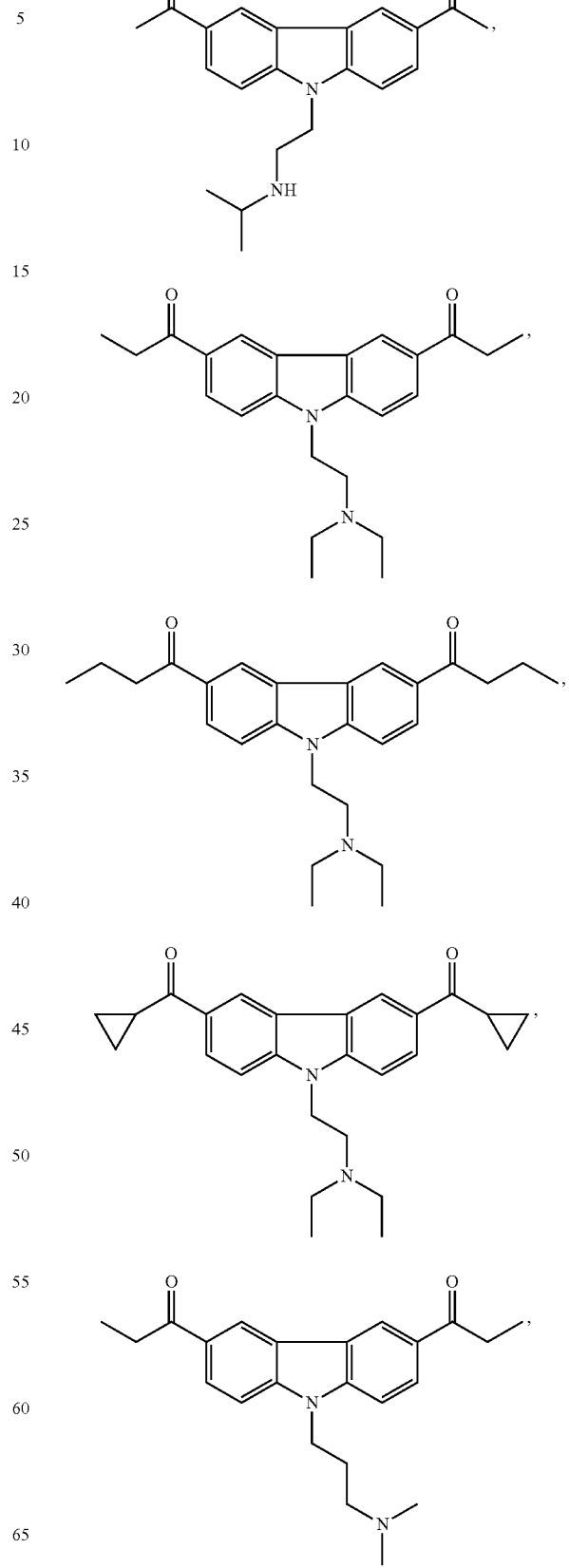

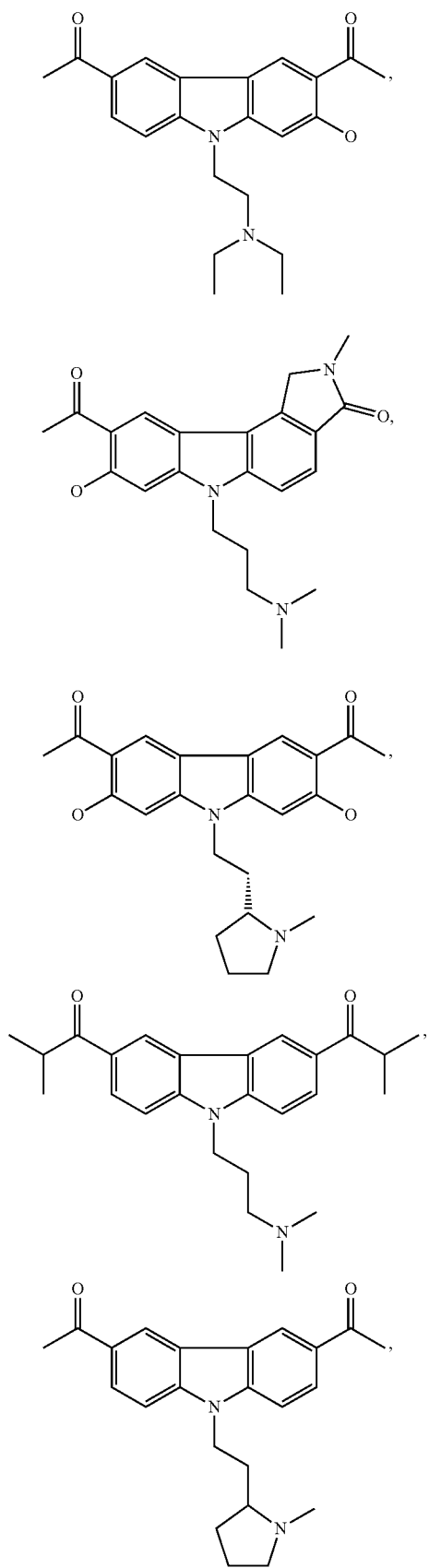
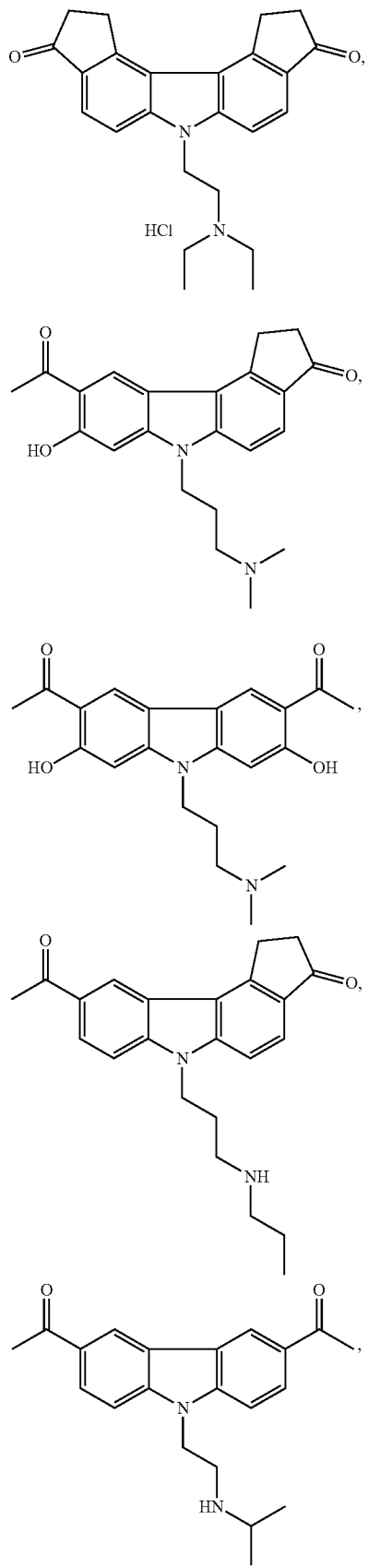

-continued

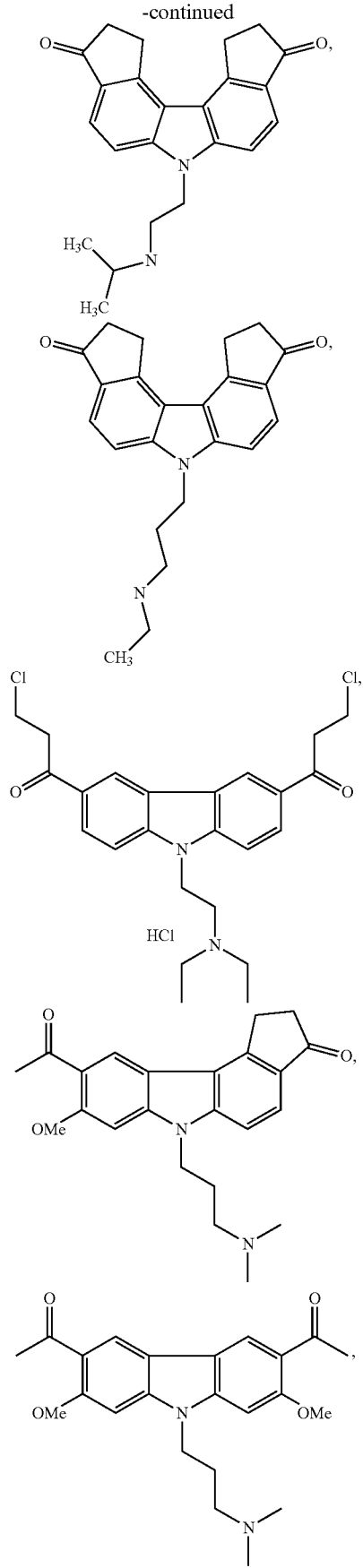
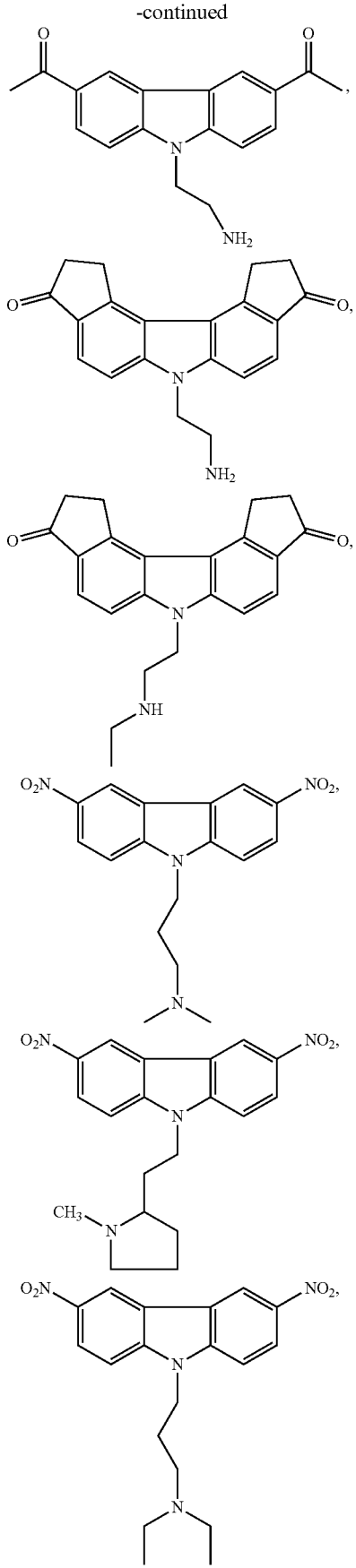

35
-continued
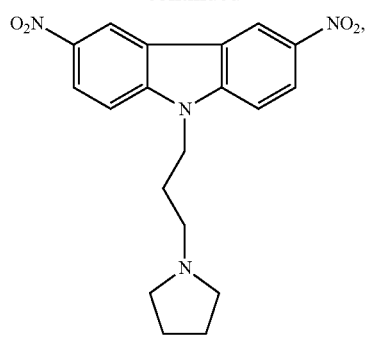
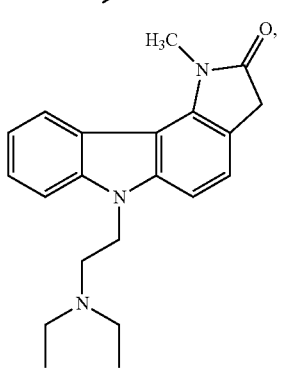
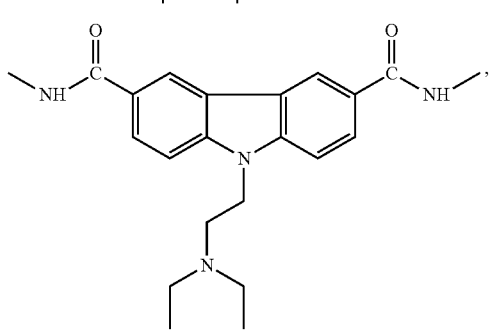
36
-continued
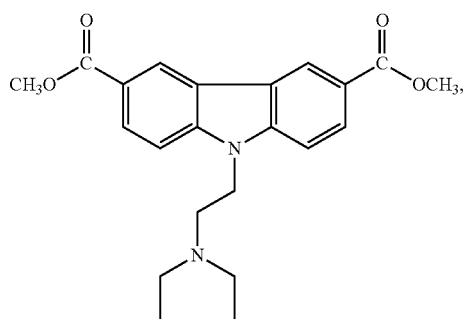
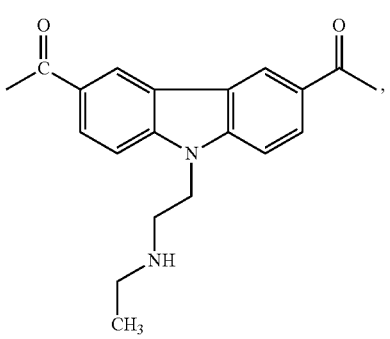
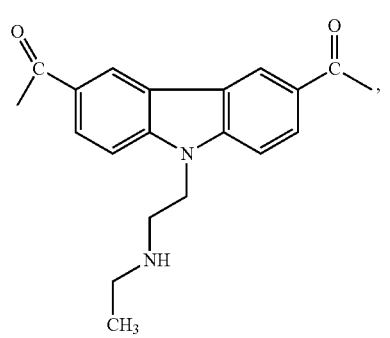
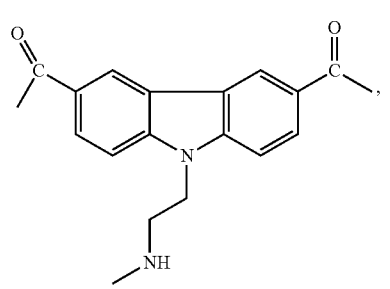
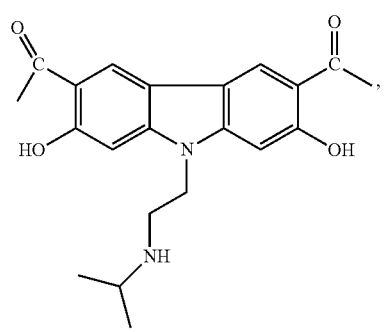

37
-continued
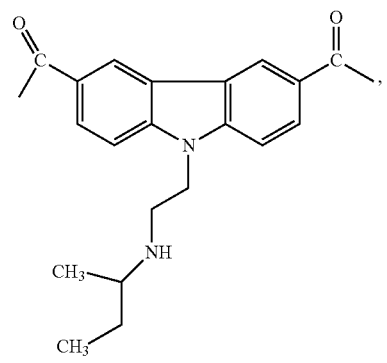
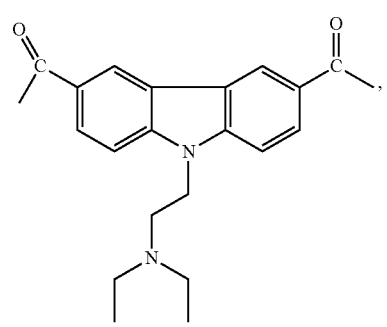
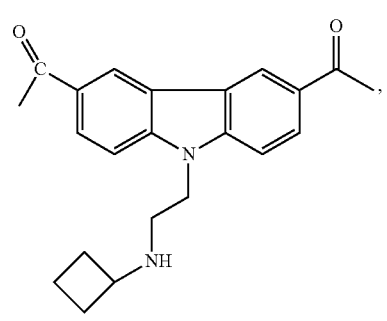
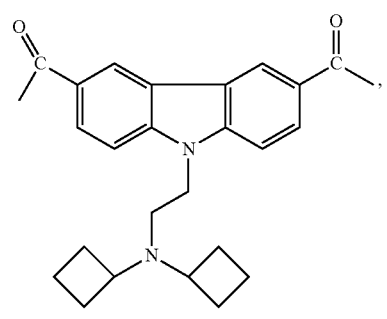
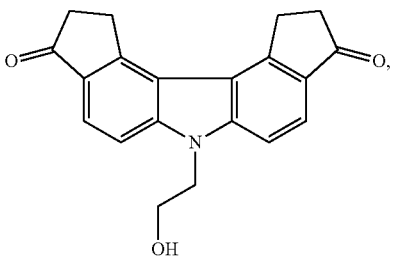
38
-continued
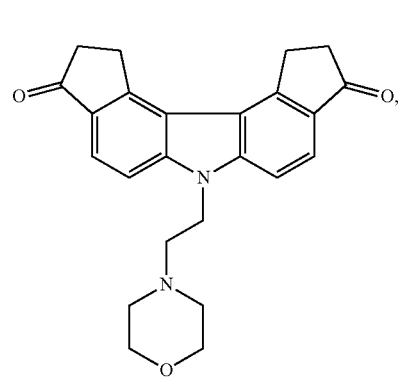
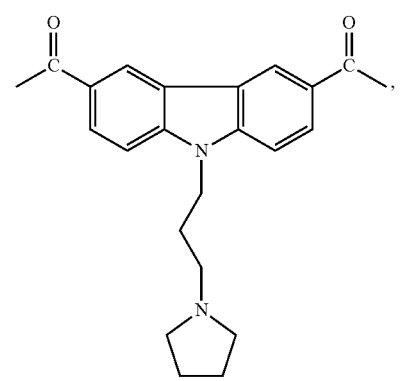
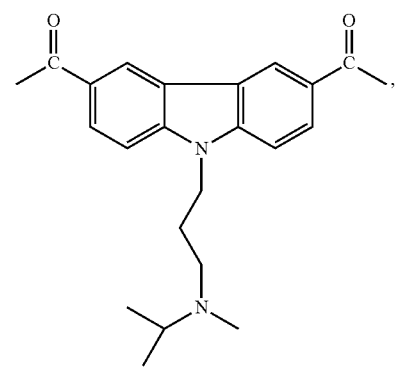
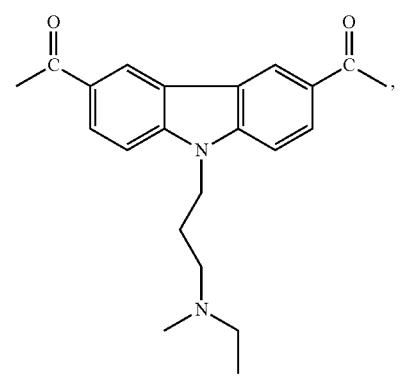

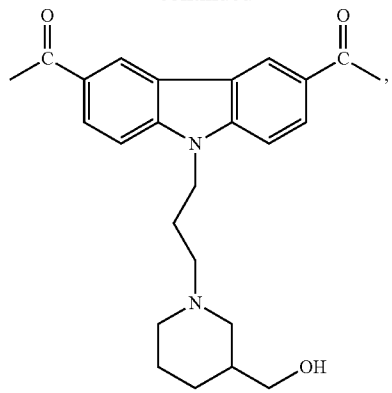
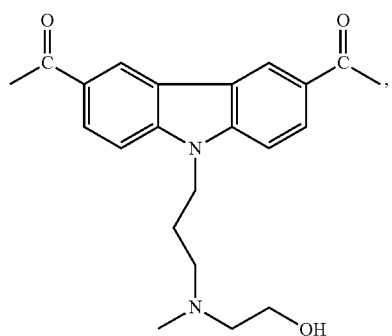
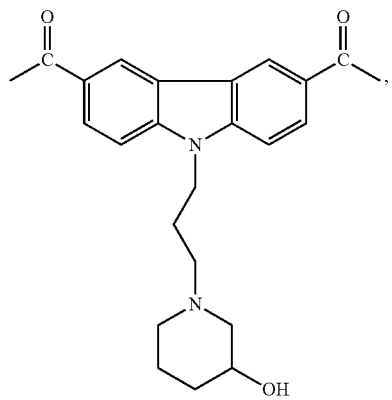
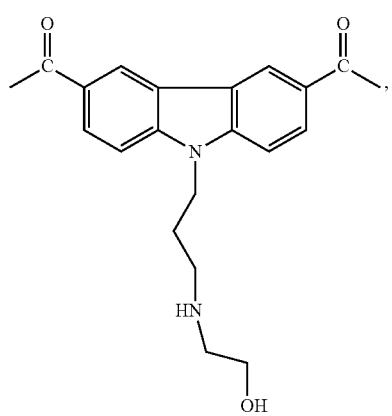
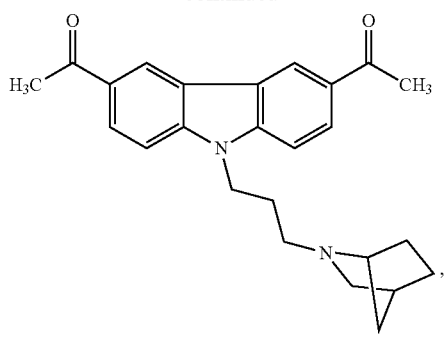
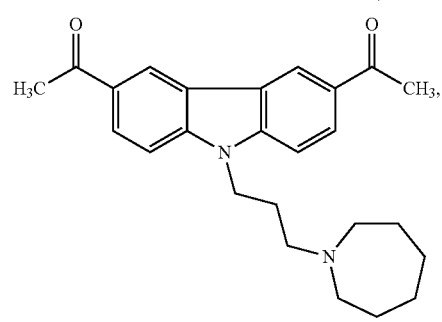
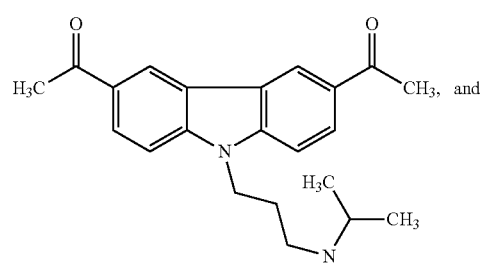
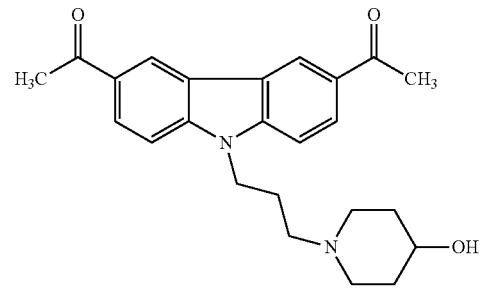
The carbozole derivative may have the following formula:
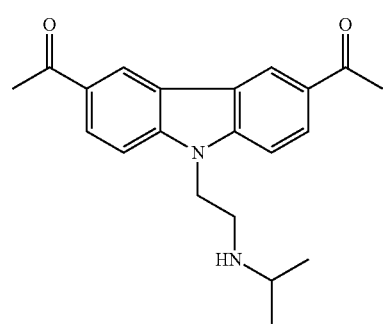 [SMILES: CC(=O)c1ccc2c(c1)c1cc(C(C)=O)ccc1n2CCNC(C)C]
The carbazole may also be selected from the group consisting of:

CBL0137
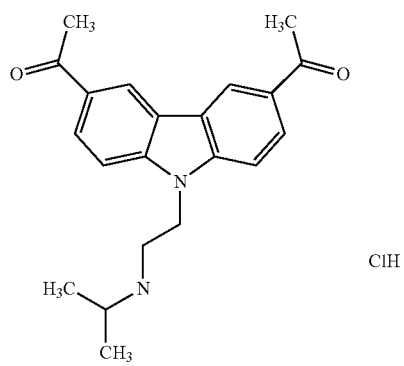
ClH
CBL0159
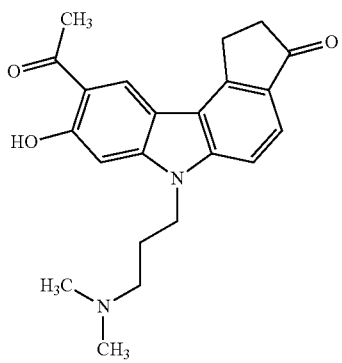
ClH
CBL0197
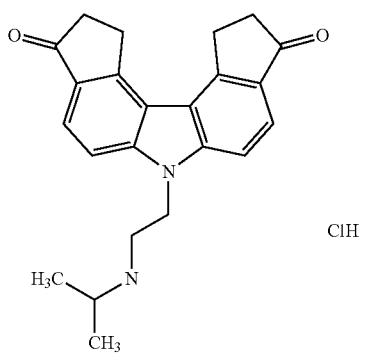
ClH
CBL0212 Chiral
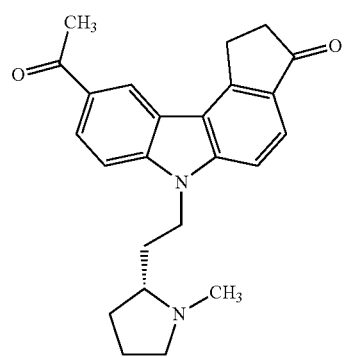
ClH
CBL0198
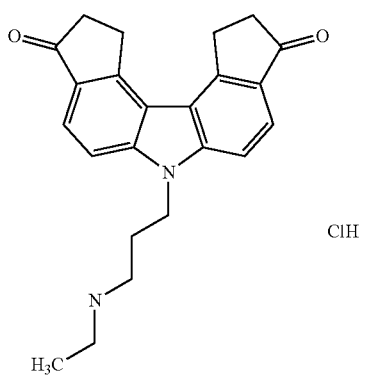
ClH
CBL0174
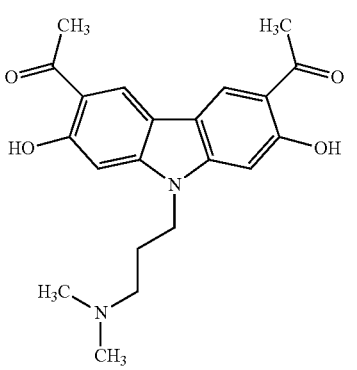
ClH and
CBL0100
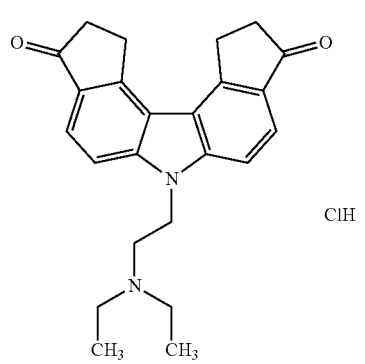
ClH
CBL0175
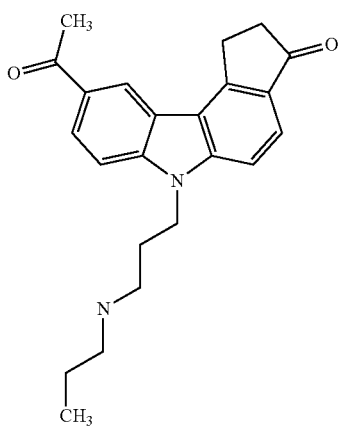
ClH
(3) Inhibitor of Transcription or Translation
The inhibitor of adaptive heat shock response may also be an inhibitor of transcription or translation. For example, the inhibitor may be actinomycin D or cycloheximide.

b. Heat Shock Response-Inducing Agent or Condition

(1) Heat Shock Response-Inducing Agent

Heat shock response may be induced in the cell with a heat shock response-inducing agent. The agent may be a protein synthesis inhibitor such as puromycin or azetidine. The agent may also be a HSP90 inhibitor such as geldanamycin (DMAG17), radicicol, or 17-AAG. The agent may also be a proteasome inhibitor such as MG132, bortezomib, or lactacystin. The agent may also be a serine protease inhibitor such as DCIC, TPCK, or TLCK. The agent may be an inflammatory mediator such as a cyclopentenone, prostaglandin, arachidonate, or phospholipase $A_2$. The agent may also be a triterpenoid such as celastrol. The agent may be a co-inducer such as a non-steroidal anti-inflammatory drug such as sodium salicylate, or indomethacin, or a hydroxylamine derivative such as bimoclomol or arimoclomol. The agent may also be a flavonoid such as quercetin or a benzylidene lactam compound such as KNK437. The agent may also be an arsenite compound or ethanol.

(2) Heating Means

Heat shock response may also be induced in the cell with a heating means. The heating means may be photoelectric, mechanical, or chemical. The heating means may be capable of delivering heat to the cell noninvasively, such as transcutaneously. The heating means may also comprise a wire, lumen, receiver, probe or a catheter, as described in U.S. Pat. Pub. No. 20070288075. The heating means may comprise optical fibers, a filament, or an implanted device. The heating means may be as described in U.S. Pat. No. 5,814,008, the contents of which are incorporated herein by reference.

The heating means may also comprise a sensor for measuring the temperature of a cell or tissue at a treatment site, and may produce a signal indicative of the temperature. The temperature may be measured with a thermocouple, a resistance temperature device, or a thermistor. The sensor may be a thermal needle sensor or a temperature probe. The temperature of the heating means may be controlled in response the signal. The temperature may be controlled by varying the amount of power supplied to energize the heat source to maintain the temperature at a predetermined level, or to prevent the temperature of the treated cell or tissue from exceeding a predetermined level.

(a) Photoelectric

The heating means may be a light emitting source such as an array of light emitting solid state devices. For example the light source may be a light emitting diode, electroluminescent device, laser, laser diode, vertical cavity emitting laser, or a filament lamp. The light may be of a specific wavelength, which may be a visible, near-infrared, or infrared wavelength. For example, the wavelength may be from 750 nm to 1 mm. The wavelength may also be 750, 760, 770, 780, 790, 800, 810, 820, 830, 840, 850, 860, 870, 880, 890, 900, 910, 920, 930, 940, 950, 960, 970, 980, 990, or 1000 nm. The wavelength may also be 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 µm. The wavelength may also be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µm. The wavelength may also be 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µm.

The light source may be an intense laser, and may comprise using a two-photon method. The laser may comprise a highly collimated beam. The light source may also be a low power, non-coherent light source. The light may also be emitted at fewer particles per square meter (i.e., at a lower fluence rate) compared to a high intensity laser. For example, the fluence may be 30-25,000 Joules. The light intensity may be less than 500 mW/cm$^2$.

The heating means may also emit microwave or radio frequency energy, as described in U.S. Pat. Nos. 6,904,323 and 5,549,638, the contents of which are incorporated herein by reference. The heating means may comprise antenna, such as in an antenna array. The heating means may also comprise an ultrasound transducer.

(b) Mechanical

The heating means may comprise a resistive element. The resistive element may be a resistive filament lamp. The heating means may also comprise a heated fluid or gas, which may be contained within a balloon, as described in U.S. Pat. Pub. No. 2007/0288075, the contents of which are incorporated herein by reference.

(c) Chemical

The heating means may comprise a chemical capable of increasing the internal temperature of the cell. For example, the chemical may comprise a dextran iron oxyhydroxide particle or iron complex. The chemical may also be gallium, indium, technetium, strontium, iodine, or other compound compatible with living tissue. The chemical may increase the internal temperature of the cell by increasing the rate of metabolism or oxidation of the chemical in the cell, such as by increasing blood oxygenation levels, as described in U.S. Pat. No. 4,569,836, the contents of which are incorporated herein by reference.

(d) Temperature

The internal temperature of the cell may be raised to at least 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100° C. The internal temperature of the cell may also be raised to between 1-38° C., 39-45° C., 45-60° C., 60-85° C., or 85-100° C. The temperature may be sufficient to impair or kill the aminoacridine-treated cell, but too low to impair or kill a normal cell that may be untreated. The temperature may also be sufficient to induce heat shock. The internal temperature of the cell may be raised for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 min, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours.

c. Administration

The compounds, chemicals, and agents described herein may be administered to a cell by absorption and diffusion into a patient's vascular system. Administration to the patient may be orally, parenterally, transdermally, or via a suppository. Administration to a cell may be by a needle attached to a syringe or by a catheter coupled to an intravenous delivery system, or topically.

3. TREATING A PATIENT

The method provided herein may be used to treat a disease or condition in a patient in need thereof. The inhibitor of adaptive heat shock response may be administered to the patient, and heat shock response may be induced in the patient either locally or generally. For example, an agent capable of inducing the heat shock response may be administered to a cell such as an infected cell or in a tumor. The heat shock response-inducing agent may also be generally administered to the patient. The internal temperature of the cell may be increased by locally applying a heating means to the cell. The patient's body temperature may also be elevated generally, such as in a physiologically-tolerated hyperthermia.

a. Cancer

Cancer or a precancerous condition may be treated by using a method disclosed herein. The cancer may be a tumor, which may be subcutaneous or cutaneous. The tumor may have a small or large volume. The tumor may be of the brain, such as a glial tumor, glioblastoma, astrocytoma, anaplastic astrocytoma, astrocytoma-oligodendroglioma, pituitary adenoma. The cancer may be a pulmonary or pleural mesothelial cancer such as lung cancer, lung carcinoma, non-small cell lung cancer, a cancer of the tracheobronchial tree, early-stage lung cancer, endo-bronchial metastatic tumor, peripheral lung cancer, or malignant pleural mesothelioma.

The cancer may also be a gastroenterological cancer such has a pre-malignant or malignant lesion located within the esophagus, stomach bile duct, or colorectum. The cancer may be and head and neck cancer, esophageal cancer, early-stage esophageal cancer, Barrett's esophagus, hilar cholangiocarcinoma, a solid lesion of the liver or pancreas, a colorectal liver metastasis, or pancreatic cancer.

The cancer may also be a urological disease such as recurrent papillary tumor, bladder cancer, superficial bladder cancer, prostate cancer, or benign prostatic hyperplasia. The cancer may also be a gynecological cancer, such as a carcinoma or dysplasia of the uterine cervix, cervical cancer, or cervical intraepithelial neoplasia.

The cancer may be a skin cancer, which may be squamous cell carcinoma (SCC), basal cell carcinoma (BCC), malignant melanoma, HIV-related Kaposi's sarcoma, Mediterranean-related Kaposi's sarcoma, basaloid follicular hamartoma, Bowen's disease, cutaneous T-cell lymphoma, or sebaceous gland hyperplasia. The cancer may also be a skin pre-malignant or malignant lesion. The cancer may also be a breast cancer such as metastatic breast cancer, a colon cancer, endometrial cancer, ocular tumor, or a head and neck cancer such as in the oral cavity, pharynx, lip carcinoma, nasal cavity, or larynx.

(1) Combination Treatment

The method for treating cancer or a precancerous condition, compound, or composition disclosed herein may be combined or co-administered with the anti-cancer treatment. The anti-cancer treatment may be the anti-cancer agent, a radiation therapy, surgery, or PDT.

(a) Anti-Cancer Treatment

The anti-cancer treatment may be a radiation therapy such as X-ray, radio frequency or microwave energy, ultrasound, radioisotope therapy, ionizing radation, external beam or teletherapy, brachytherapy or sealed source radiotherapy, or unsealed source radiotherapy. The anti-cancer treatment may also be a surgery such as debulking surgery, cryotherapy, or surgical excision.

(2) Photodynamic Therapy

The PDT may comprise irradiating the aminoacridine treated cell, which may also be treated with the photosensitizing agent, with visible light. The light may be of a particular wavelength, and may activate the photosensitizing agent. The activated photosensitizing agent may generate a singlet oxygen or radical, which may impair or kill the cell. The PDT may be as described in U.S. Pat. Nos. 6,899,723 and 6,693,093, the contents of which are incorporated herein by reference.

b. Treating a Non-Malignant Indication

A non-malignant indication in a patient in need thereof may be treated by using the method. The indication may be a skin condition such as psoriasis, viral warts, or hair removal. The condition may also an ocular condition such as age-related macular degeneration, subfoveal choroidal vascularization, pathological myopia, ocular histoplasmosis syndrome, or choroidal neovascular disease. The indication may also be a cardiovascular disease such as an atherosclerotic plaque, intimal hyperplasia, atherosclerosis or vulnerable plaque, or restenosis.

c. Treating an Infection

An infection in a patient in need thereof may be treated using the method. The infection may be a viral infection such as by a herpesvirus, influenza, human immunodeficiency virus, or hepatitis A, B, or C. The infection ay also be a bacterial infection, such as by Chlamydia, tuberculosis, or mycoplasma.

The infection may also be by a eukaryotic parasite, such as a fungus, Giardia, Toxoplasma, or trypanosome. The fungus may be a yeast. The trypanosome may cause malaria and may be a Plasmodium, or it may be leishmania.

d. Treating an Inflammation-Associated Disease

An inflammation-associated disease or condition may also be treated using the method. The inflammation may be chronic, an autoimmune disease, allergy, asthma, septic shock, graft versus host disease, surgical wound, burn, or ischemic condition.

4. METHOD OF SCREENING

Also provided herein is a method for screening for a compound capable of modulating adaptive heat shock response in a cell when the compound is combined with inducing heat shock response. The method may comprise inducing heat shock response in a population of cells and contacting the population with a test compound. The number of cells that die in the population compared to a control may be indicative of a compound that modulates adaptive heat shock response.

The cells in the population may also comprise a heat shock response-induced reporter. The method may further comprise measuring the level of the reporter. The level of the reporter compared to a control may be indicative of a compound that modulates adaptive heat shock response. The reporter may comprise a transcript of a HSP70 gene such as HSP70A1 or HSP70'B. The reporter may also comprise a HSP70 protein. The reporter may also comprise a vector comprising a heat shock response-induced promoter operably linked to a reporter gene. The reporter gene may encode a detectable marker, which may be luciferase, green fluorescent protein, yellow fluorescent protein, red fluorescent protein, or chloramphenicol acetyltransferase.

5. COMPOSITION

The present invention relates to a composition that may comprise an inhibitor of adaptive heat shock response. The composition may also comprise a heat shock response-inducing agent. The composition may also comprise a therapeutic agent, which may be an anti-cancer agent or a photosensitizing agent. The composition may be used in a treatment by inducing heat shock response in a composition-treated cell, which may impair or kill the cell.

a. Anti-Cancer Agent

The anti-cancer agent may be any pharmacological agent or compound that induces apoptosis. The pharmacological agent or compound may be, for example, a small organic molecule, peptide, polypeptide, nucleic acid, or antibody.

The anti-cancer agent may be a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

The cytotoxic agent may be: an alkylating agent (including nitrogen mustard, ethylenimine derivatives, alkyl sulfonates, nitrosoureas or triazene): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, or temozolomide; antimetabolite (including a folic acid antagonist, pyrimidine analog, purine analog and adenosine deaminase inhibitor): methotrexate, 5-fluorouracil, floxuridine, cytarabine, 6-mercaptopurine, 6-thioguanine, fludarabine phosphate, pentostatine, and gemcitabine; a natural product or its derivative (for example, vinca alkaloid, antitumor antibiotic, enzyme, lymphokine or epipodophyllotoxin): vinblastine, vincristine, vindesine, bleomycin, dactinomycin, daunorubicin, doxorubicin, epirubicin, idarubicin, ara-c, paclitaxel (Taxol®), mithramycin, deoxyco-formycin, mitomycin-c, 1-asparaginase, interferon (preferably IFN-a), etoposide, or teniposide. The cytotoxic agent may also be navelbene, CPT-11, anastrazole, letrazole, capecitabine, reloxafine, cyclophosphamide, ifosamide, or droloxafine.

The cytotoxic agent may also be a microtubule-affecting agent, which may interfere with cellular mitosis. The microtubule-affecting agent may be: allocolchicine (NSC 406042), halichondrin B (NSC 609395), colchicine (NSC 757), a colchicine derivative (e.g., NSC 33410), dolastatin 10 (NSC 376128), maytansine (NSC 153858), rhizoxin (NSC 332598), paclitaxel (Taxol®, NSC 125973), a Taxol® derivative (e.g., NSC 608832), thiocolchicine (NSC 361792), trityl cysteine (NSC 83265), vinblastine sulfate (NSC 49842), vincristine sulfate (NSC 67574), natural or a synthetic epothilone such as epothilone A, epothilone B, or discodermolide (see Service, (1996) Science, 274:2009), estramustine, nocodazole, MAP4, or the like. The microtubule-affecting agent may also be as described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem. 271:29807-29812.

The cytotoxic agent may also be: epidophyllotoxin; an antineoplastic enzyme; a topoisomerase inhibitor; procarbazine; mitoxantrone; a platinum coordination complex such as cis-platin or carboplatin; a biological response modifier; growth inhibitor; antihormonal therapeutic agent; leucovorin; tegafur; or haematopoietic growth factor.

The cytostatic agent may be a hormone or steroid (including synthetic analog): 17.alpha.-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, or zoladex.

The cytostatic may also be an antiangiogenic such as a matrix metalloproteinase inhibitor, or other VEGF inhibitor such as an anti-VEGF antibody or a small molecule such as ZD6474 and SU6668. The cytostatic agent may also be an anti-Her2 antibody from Genentech, a EGFR inhibitor such as EKB-569 (an irreversible inhibitor), or Imclone antibody C225, which may be immunospecific for the EGFR, or a src inhibitor.

The cytostatic agent may also be Casodex® (bicalutamide, Astra Zeneca) which may render an androgen-dependent carcinoma non-proliferative; the antiestrogen Tamoxifen®, which may inhibit the proliferation or growth of estrogen dependent breast cancer; or an inhibitor of the transduction of a cellular proliferative signal, such as an epidermal growth factor inhibitor, Her-2 inhibitor, MEK-1 kinase inhibitor, MAPK kinase inhibitor, PI3-kinase inhibitor, Src kinase inhibitor, or PDGF inhibitor. The anti-cancer may also be a compound listed in Table 1 of U.S. Provisional Application No. 61/102,913, filed Oct. 6, 2008, the contents of which are incorporated herein by reference.

b. Photosensitizing Agent

The photosensitizing agent may be a compound that is absorbed by the cell, and that when exposed to light is activated and causes a substance to be produced that impairs or kills the cell. The substance may be a singlet oxygen or radical. The photosensitizing agent may absorb light with a wavelength of 500 nm to 1.1 μm. The photosensitizing agent may be one as disclosed in U.S. Pat. No. 6,693,093 or 7,018,395, the contents of which are incorporated herein by reference.

For example, the photosensitizing agent may be a green porphyrin; a polypyrrolic macrocyclic photosensitive compound that is hydrophobic; an angelicin; a lipofuscin; a photosystem II reaction center; a D1-D2-cyt b-559 photosystem II reaction center; a chalcogenapyrillium dye; a chlorine; a chlorophyll; a coumarin; a cyanine; a DNA-related compound such as adenosine, cytosine, 2'-deoxyguanosine-5'-monophosphate, deoxyribonucleic acid, guanine, 4-thiouridine; 2'-thymidine 5'-monophosphate, thymidylyl(3'-5')-2'-deoxyadenosine, thymidylyl(3'-5')-2'-deoxyguanosine, thymine, or uracil; a drug such as adriamycin; afloqualone, amodiaquine dihydrochloride, chloroquine diphosphate, chlorpromazine hydrochloride, daunomycin, daunomycinone, 5-iminodaunomycin, doxycycline, furosemide, gilvocarcin M, gilvocarcin V, hydroxychloroquine sulfate, lumidoxycycline, mefloquine hydrochloride, mequitazine, merbromin (mercurochrome), primaquine diphosphate, quinine sulfate, or tetracycline hydrochloride; a flavin or related compound such as alloxazine, flavin mononucleotide, 3-hydroxyflavone, limichrome, limitlavin, 6-methylalloxazine, 7-methylalloxazine, 8-methylalloxazine, 9-methylalloxazine, 1-methyl limichrome, methyl-2-methoxybenzoate, 5-nitrosalicyclic acid, proflavine, or riboflavin; a fullerene; a metalloporphyrin; metallophthalocyanines; a methylene blue derivative; a naphthalimide; a naphthalocyanine; a natural compound such as bis(4-hydroxy-3-methoxyphenyl)-1,6-heptadiene-3,5-dione, 4-(4-hydroxy-3-methoxyphenyl)-3-buten-2-one, N-formylkynurenine, kynurenic acid, kynurenine, 3-hydroxykynurenine, DL-3-hydroxykynurenine, sanguinarine, berberine, carmine, or 5; 7; 9(11); 22-ergostatetraene-3β-ol; a nile blue derivative; a NSAID (nonsteroidal anti-inflammatory drug); aperylenequinone; a phenol; a pheophorbide; a pheophytin; a photosensitizer dimer or conjugate; a phthalocyanine; a porphycene; a porphyrin; a psoralen; a purpurin; a quinone; a retinoid; a rhodamine; a thiophene; a verdins; a vitamin; or a xanthene dye (Redmond and Gamlin, Photochem. Photobiol., 70(4):391-475 (1999)).

c. Formulation

The composition may further comprise one or more pharmaceutically acceptable additional ingredient(s) such as alum, stabilizers, antimicrobial agents, buffers, coloring agents, flavoring agents, adjuvants, and the like.

The composition may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

The composition may also be liquid formulations including, but not limited to, aqueous or oily suspensions, solutions, emulsions, syrups, and elixirs. The composition may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

The composition may also be formulated as suppositories, which may contain suppository bases including, but not limited to, cocoa butter or glycerides. The composition may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. The composition may also be formulated transdermal formulations comprising aqueous or nonaqueous vehicles including, but not limited to, creams, ointments, lotions, pastes, medicated plaster, patch, or membrane.

The composition may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

The composition may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes may be used such as those described in U.S. Pat. No. 5,077,211, U.S. Pat. No. 4,621,023 or U.S. Pat. No. 4,508,703, which are incorporated herein by reference. A composition intended to target skin conditions can be administered before, during, or after exposure of the skin of the mammal to UV or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

d. Dosage

A therapeutically effective amount of an agent required for use in therapy varies with the nature of the condition being treated, the length of time that activity is desired, and the age and the condition of the patient, and is ultimately determined by the attendant physician. The desired dose may be conveniently administered in a single dose, or as multiple doses administered at appropriate intervals, for example as one, two, three, four or more subdoses per day. Multiple doses often are desired, or required.

When given in combination with other therapeutics, the composition may be given at relatively lower dosages. In addition, the use of targeting agents may allow the necessary dosage to be relatively low. Certain compositions may be administered at relatively high dosages due to factors including, but not limited to, low toxicity, high clearance, low rates of cleavage of the tertiary amine. As a result, the dosage of a composition may be from about 1 ng/kg to about 200 mg/kg, about 1 μg/kg to about 100 mg/kg, or about 1 mg/kg to about 50 mg/kg. The dosage of a composition may be at any dosage including, but not limited to, about 1 μg/kg-1 mg/kg, or 1 mg/kg-100 mg/kg.

The present invention has multiple aspects, illustrated by the following non-limiting examples.

Example 1

Inhibiting Adaptive Heat Shock Response Combined with Inducing Heat Shock Response can Induce Cell Death This example demonstrates that the efficacy of heat shock-targeted therapy can be greatly facilitated by agents that block the induction of adaptive heat shock response, thus preventing tumor cells from mobilizing natural resistant mechanism via recruitment of inducible chaperones. Adaptive heat shock response can be selectively blocked by suppressing HSF-1, the major mediator of inducible heat shock-triggered transcription. Adaptive heat shock response-inhibiting agents could be used in combination with heat shock-inducing compounds or conditions, which should lead to their enhanced cytotoxicity. This cytotoxicity is expected to be more pronounced in tumor than in normal cells due to higher degree of tumor cell dependence on shaperones.

This example also demonstrates that the anti-malaria drug quinacrine (QC), its related compound 9-aminoacridine (9AA) and other chemicals belonging to the family of carbazoles (CZ), act as DNA-intercalating non-genotoxic agents that affect function of certain classes of gene promoters that are inducible by activating signal transduction pathways. Testing heat shock response of cells in the presence of these compounds demonstrated that these compounds can suppress HSF-1-mediated transcription in a dose dependent manner regardless of the treatment or agent used to induce heat shock response.

Quinacrine and 9AA were added to tumor cells in culture to examine the effect of these compounds on hsp70 activation in response to heat shock-inducing treatment. The heat shock response was induced by using the known proteasome inhibitors MG132 and Bortezomib, the HSP90 inhibitor DMAG17 (Geldanamycin), and heat treatment (42-45° C., 10-60 min). To monitor heat shock response an inducible isoform of Hsp70 was detected by Western immunoblotting using an antibody that recognizes an inducible form of the HSP70 protein, and by Northern hybridization using a probe that specifically recognizes mRNAs of the inducible HSP70A1 and HSP70B' genes, but does not recognize a mRNA that encodes constitutively-expressed HSC70 protein. QC and 9AA prevented HSP70 protein induction (FIG. 1A). Quinacrine and 9AA did not affect the ability of MG132 or Bortezomib to inhibit proteasome activity (FIG. 1B), indicating that the effects of QC and 9AA were not associated with inactivation of the heat-shock-inducing treatments. Moreover, inducible HSP70 transcripts accumulated in cells treated with the above heat shock response-inducing treatments, but transcription was blocked in the presence of quinacrine and 9AA (FIG. 2). In addition to aminoacridines, a similar effect was observed by treating cells with emetine, which is a general inhibitor of translation (FIG. 2). This confirms that the observed effect of QC and 9AA was due to a lack of heat shock protein induction.

FIG. 1 shows that QC and 9AA prevented HSP70 protein induction in cells treated with proteasome inhibitors. Protein extracts from HeLa cells treated with 5 μM of proteasome inhibitor MG132 for 8 h alone or in combination with QC or 9AA were examined using an antibody to the inducible form of HSP70 and to Pirin (gel loading control) (FIG. 1A). Results of an in vitro proteasome activity assay from extracts of cells treated with MG132 alone or in combination with quinacrine and 9AA show that QC and 9AA do not affect inhibition of proteasomes by MG132 (FIG. 1B).

FIG. 2 shows that QC and 9AA inhibited transcription of HSP70 gene in response to proteasomes inhibitors. 10 μg of total RNA from HeLa cells were treated for 5 h with 0.1 μM of Bortezomib (Brtz), or 5 mM of MG132 (MG) alone or in combination with 20 mM of QC (Quin), 20 μM of 9AA, or 1 μM of emetine (EM). The results were analyzed by Northern blotting with a HSP70A1/B'-specific hybridization probe. GAPDH was a RNA loading control. Hsp70(x) indicates the induction of HSP70 transcription.

Figure 3:
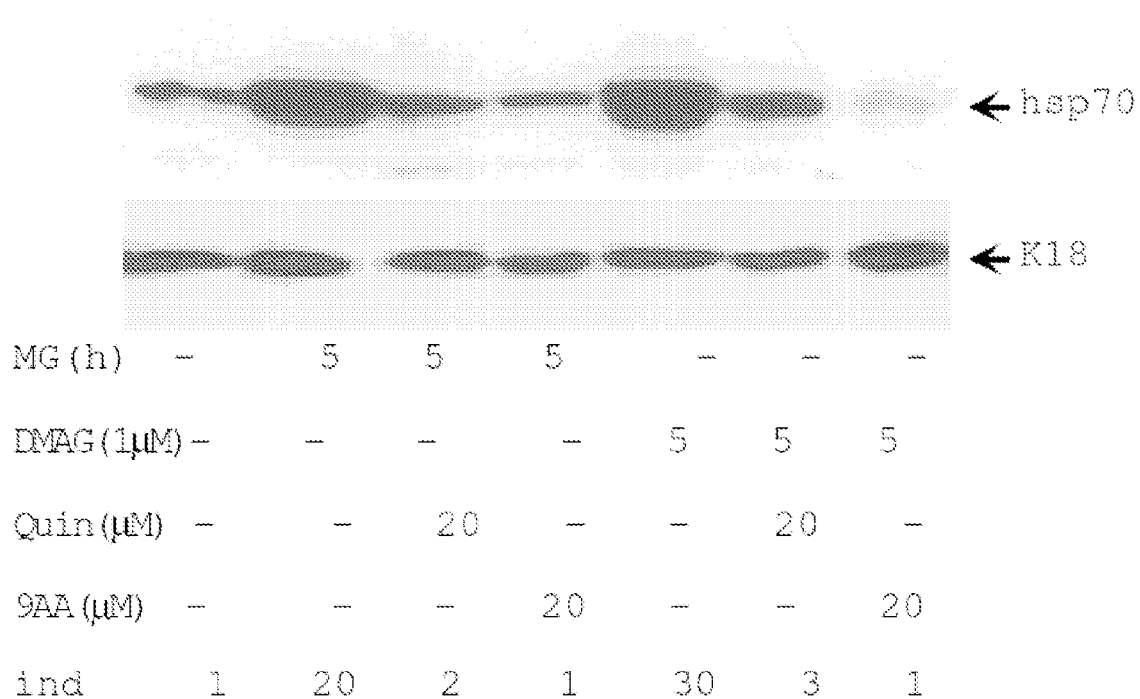
FIG. 3 shows that DMAG17-induced HSP70 synthesis is sensitive to QC and 9AA.

FIG. 3 shows that DMAG17-induced HSP70 synthesis was sensitive to QC and 9AA. Immunoblotting with anti HSP70 antibodies of 10 μg of protein extracts from HeLa cells treated 5 h with 5 μM of MG132 (MG) or DMAG17 alone, or in combination with quinacrine (Quin) or 9AA. Relative induction of HSP70 expression (ind) is indicated (results of densitometry).

Figure 4:
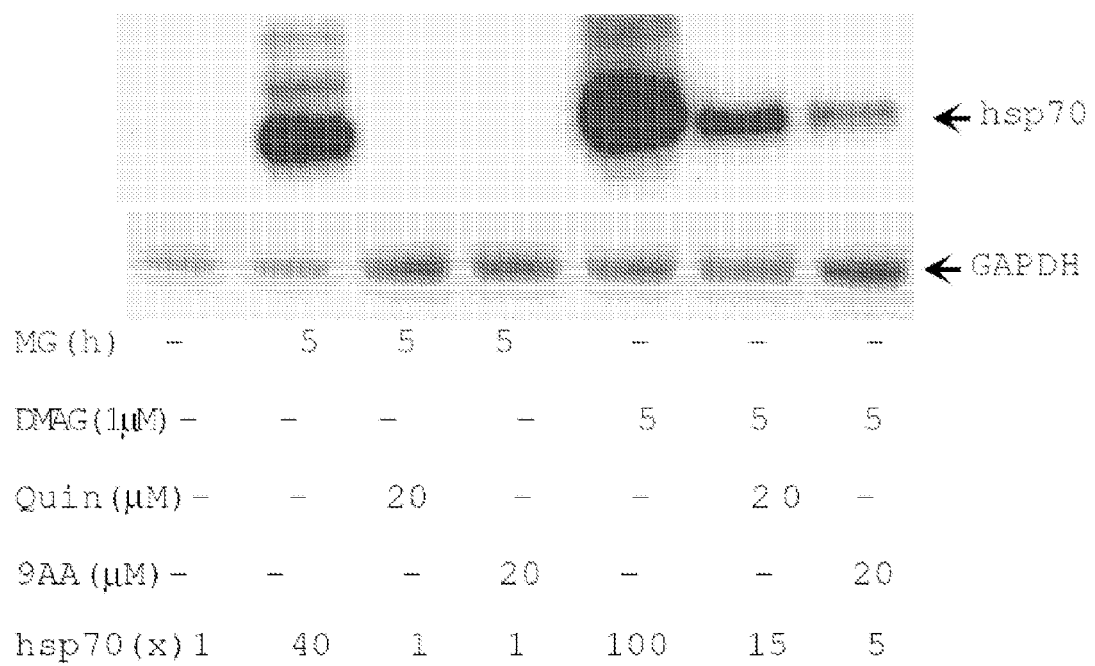
FIG. 4 shows that QC and 9AA suppress transcription of HSP70A1/B' gene induced by DMAG17 and MG132.

FIG. 4 demonstrates that QC and 9AA suppressed transcription of the HSP70A1/B' gene induction by DMAG17 and MG132, as shown by Northern hybridization of 10 μg total RNA from HeLa cells treated with 1 μM of DMAG17 5 h alone or in combination with 9AA. GAPDH was used as an RNA loading control. Hsp70(x) indicates relative induction of HSP70 transcription.

Figure 5:
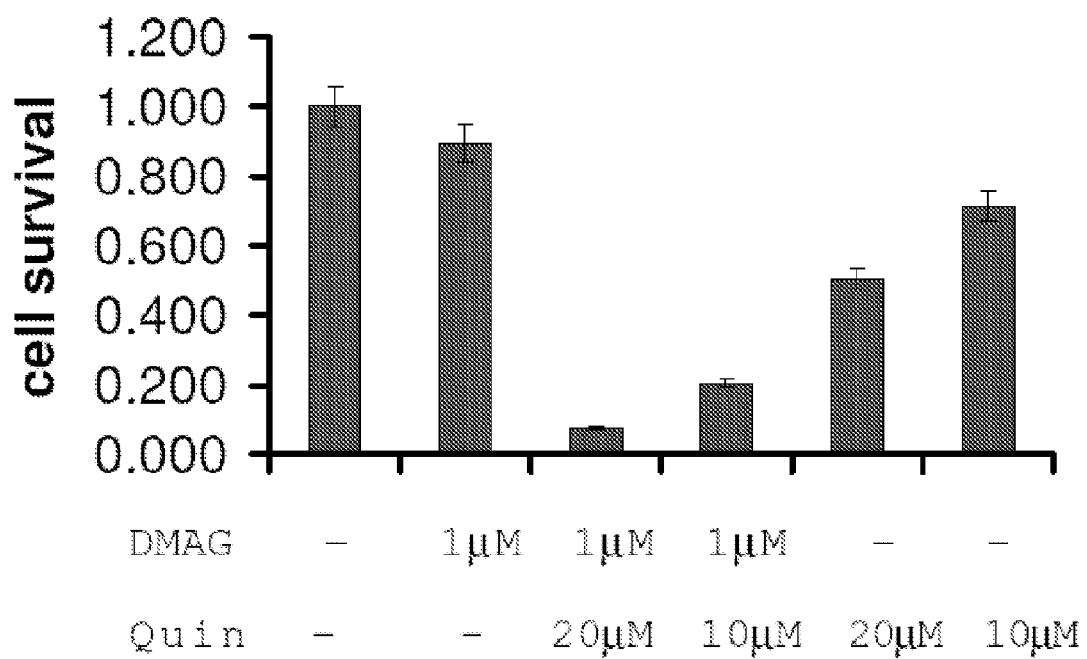
FIG. 5 shows the toxic effect of DMAG17 combined with QC in HeLa cells.

FIG. 5 demonstrates the toxic effect of drug combination in HeLa cells, as shown by the results of a colony forming assay of HeLa cells treated 6 h with the proteotoxic drug DMAG17 (1 μM) in combination with variable concentrations of quinacrine (10 or 20 μM). Cells were harvested, diluted 1:50 and assayed for colony formation. Numbers of colonies were estimated with bromphenol blue staining after 7 days of growth and fixation with 10% formaldehyde. Data are the average of three experiments. The heat shock-inducing agents and QC show synergistic cytotoxicity.

Figure 6:
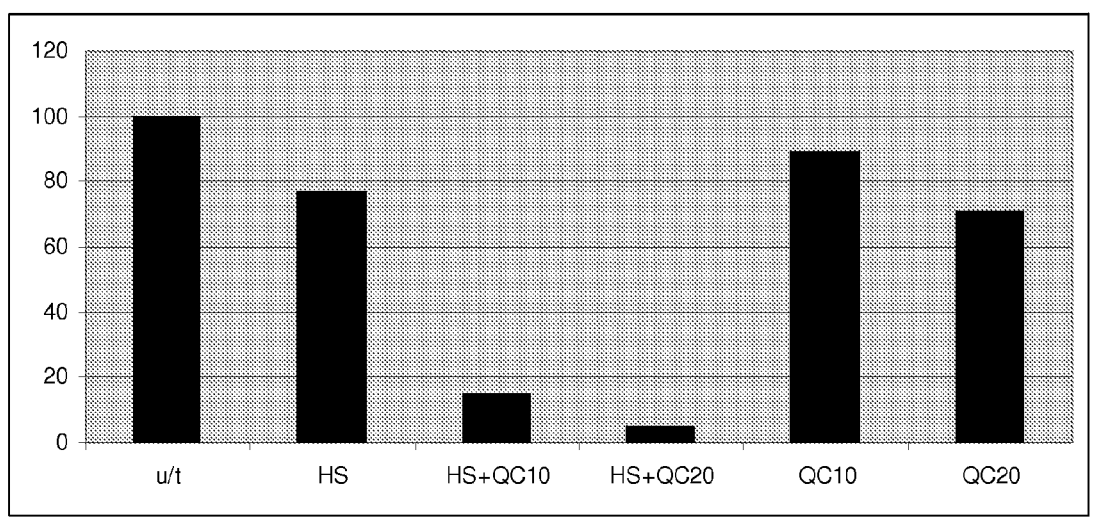
FIG. 6 shows the toxic effect of heat shock treatment (43° C., 30 min) combined with QC.

FIG. 6 shows results of an experiment similar to that shown in FIG. 5, but heat shock treatment (43° C., 30 min) was used instead of DMAG17. Synergistic cytotoxicity was observed when QC was combined with heat.

FIG. 7 shows that the heat sensitivity of tumor cells, but not normal cells, was increased upon treatment with QC and CZ (compound CBL0137). RCC45 (renal cell carcinoma cells) and NKE-hTERT (normal kidney epithelial cells, immortalized with telomerase transduction) were treated with different concentrations of QC or compound CBL0137 and then immediately placed in a water bath at 45° C. (suspended in culture media). The time of incubation in the water bath is shown by different shades. After heating, cells were plated in 96 well plates and incubated for 24 h in the presence of drug and then an additional 48 h in drug free medium. Cell viability was assessed by Cell Titer Blue staining (Alamar Blue, Promega).

Figure 8:
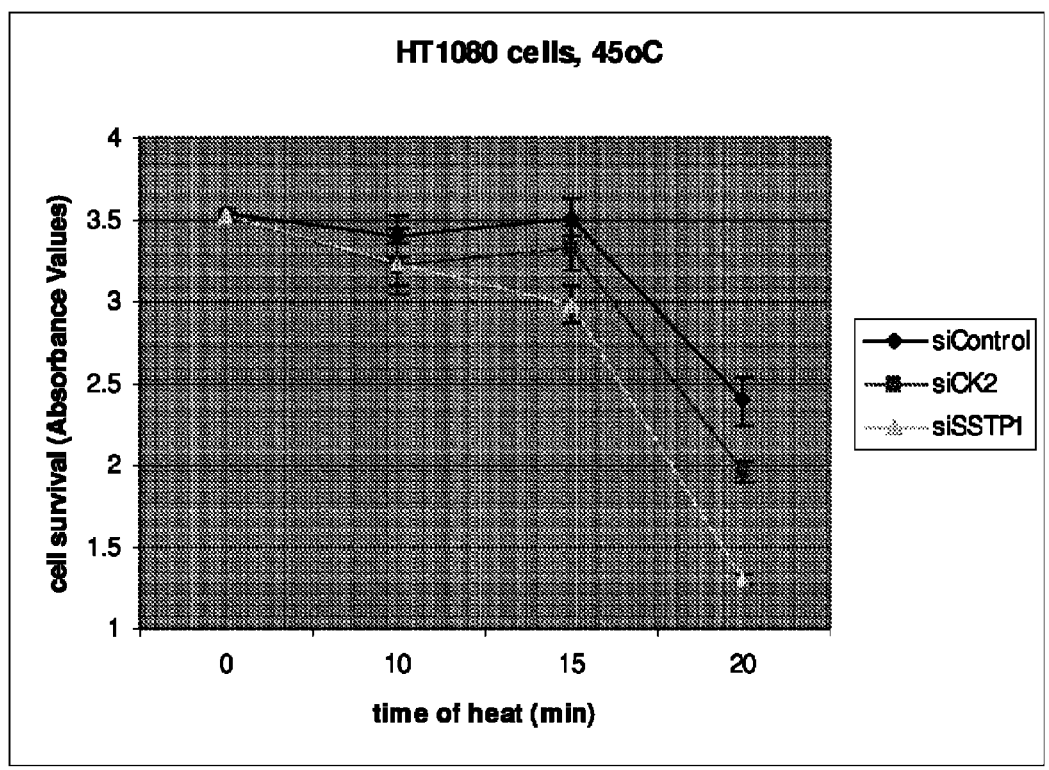
FIG. 8 shows that siRNA-mediated knockdown of a component of the FACT nuclear complex, SSPT1, and FACT kinase CKII, increases cell sensitivity to heat shock.

FIG. 8 shows that siRNA-mediated knockdown of a component of the FACT nuclear complex, SSPT1, and FACT kinase CKII, increased cell sensitivity to heat shock. HT1080 cells were transfected with siRNA pools designed against protein casein kinase II (CKII), SSPT1 and GAPDH (control) (Dharmacon) according to manufacturer's protocol. 24 h later, all cells were split into 6 well plates. After an additional 24 h, cells in plates were put heated up to 45° C. for 10, 15 and 20 minutes in a water bath. Cell viability was assessed 48 h after heating by the Cell Titer Blue assay (Promega).

These results indicate that combined treatment of tumor cells by non-toxic or marginally toxic heat shock response-inducing agents in the presence of non-toxic or mildly toxic concentrations of the compounds inhibiting HSF-1-mediated transcription result in synergistic cytotoxicity which is more prevalent for tumor than for normal cells. The molecular mechanism of inhibition of HSF-1-mediated transcription by QC, 9AA and CZ compounds is associated with their ability to inhibit of activity of the nuclear chromatin-remodeling complex FACT, which is presumably essential for JSF-1 and NF-kB-driven transcription (FIG. 8).

Example 2

Aminoacridines Prevent Activation of hsp70 in Response to Proteasome Inhibition

This example indicates that aminoacridines prevent hsp70 activation in response to proteasome inhibition. Upregulation of the inducible form of hsp70 is a hallmark of HSR following proteotoxic stress, such as that generated by proteasome inhibition. The effect of several anti-malaria drugs on synthesis of hsp70 activated by inhibition of proteasomes by the small molecule inhibitor MG132 was tested in cultured HeLa cells. Emetine and quinacrine (QC) suppressed hsp70 synthesis in response to MG132 (FIG. 9A). 9-aminoacridine (9AA), which is closely related in structure to QC, had a similar inhibitory effect on MG132-induced hsp70 expression (FIG. 9B).

Emetine is an inhibitor of general translation; therefore, its ability to suppress inducible hsp70 synthesis is likely a reflection of this property. However, QC and 9AA had no effect on overall protein synthesis (as shown by $^{35}$S-methionine and $^{35}$S-cysteine incorporation) at concentrations that were sufficient for complete suppression of hsp70 induction (FIG. 9C). This indicates that these aminoacridine-based compounds suppress inducible hsp70 synthesis through a different, more specific, mechanism. Neither QC nor 9AA affected the ability of MG132 to inhibit proteasome activity (FIG. 9D). Therefore, the drugs do not block hsp70 induction simply by interfering with the generation of proteotoxic stress via proteasome inhibition.

The inhibitory effects of QC on hsp70 induction were detectable at the mRNA level as shown by Northern hybridization of RNA from HeLa cells treated with MG132 or another proteasomal inhibitor, bortezomib, with or without QC (FIG. 9E). The hybridization probe used in this experiment was specific to the inducible hsp70A1 mRNA and did not recognize the mRNA encoding the constitutive hsc70 protein. The results indicated that QC suppressed accumulation of hsp70 mRNA under conditions of proteasome inhibition. This effect was due to repression of transcription rather than stimulation of hsp70 mRNA degradation since addition of QC after the induction of HSR had no effect on hsp70 mRNA abundance. The inhibitory effect of QC and 9AA on inducible gene expression was not universal. For example, ZnCl$_2$-induced activation of metallothionein gene transcription was not affected by these compounds under conditions at which they abolished induction of hsp70 mRNA (FIG. 9F). Moreover, QC and 9AA both caused strong induction of transcription of p53 target genes.

Example 3

Figure 10:
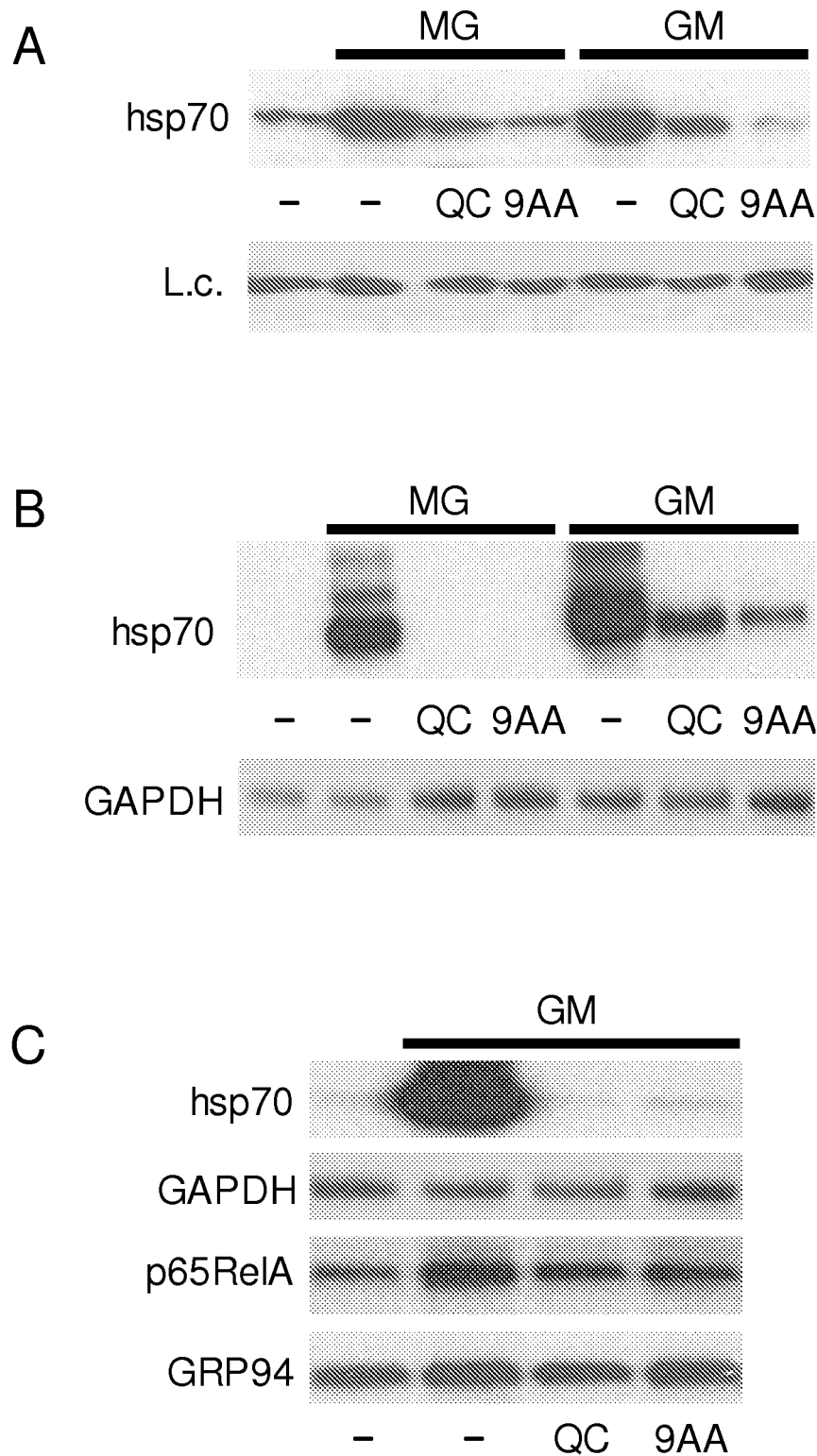
FIG. 10 shows that HSR induction by either MG132, 17-DMAG or heat shock is sensitive to aminoacridines.
Figure 10:
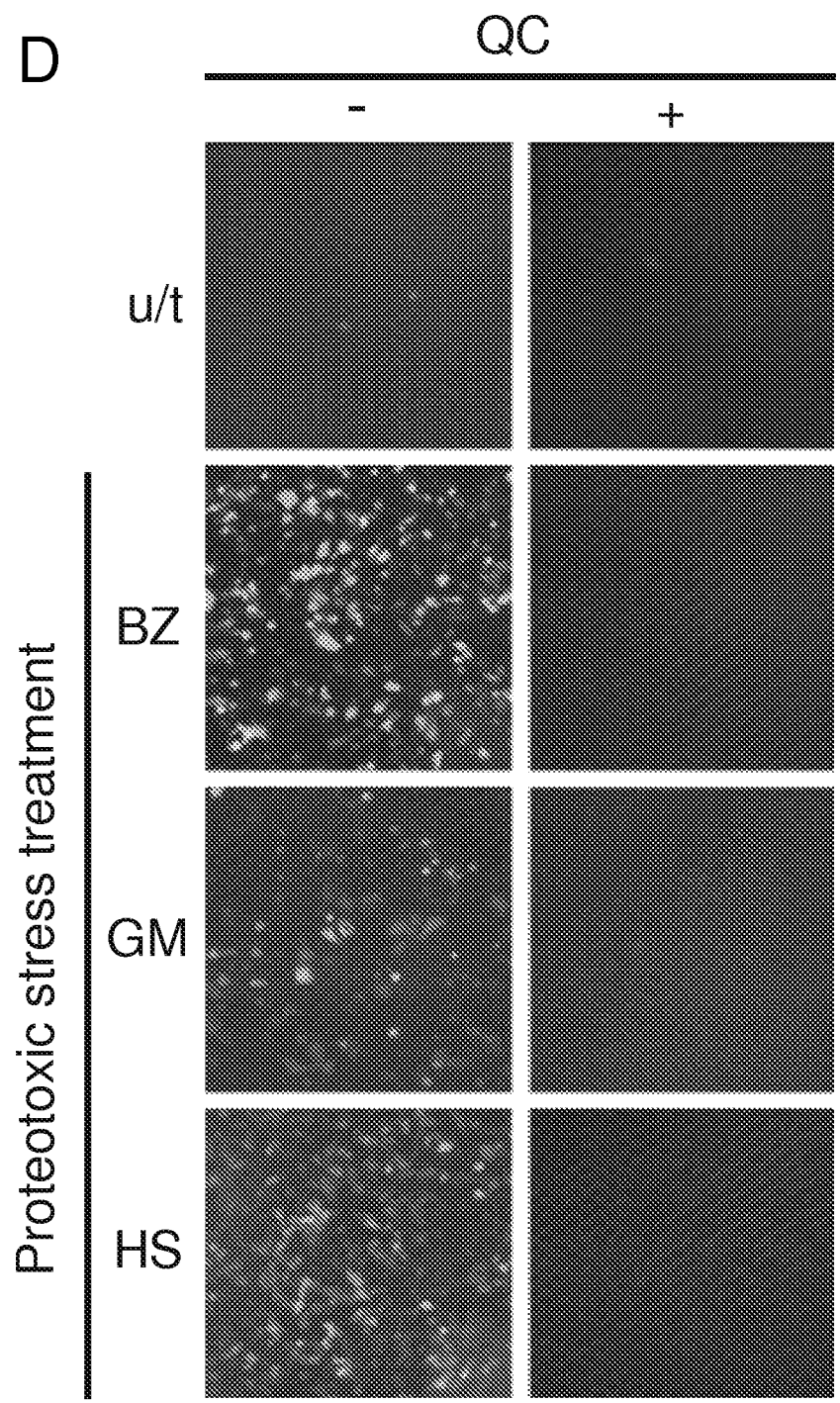

Quinacrine Blocks Induction Of Heat Shock Response by hsp90 Inhibition Or Hyperthermia This example demonstrates that quinacrine blocks the heat shock response induced by hsp90 inhibition or hyperthermia. Functional inactivation of hsp90 by geldanamycin or its derivative 17-DMAG induces proteotoxic stress and activates HSR including synthesis of hsp70. As shown in FIG. 9 for proteotoxic stress induced by proteasome inhibitors, QC and 9AA also suppressed hsp70 induction in response to hsp90 inhibition and this occurred at the transcriptional level (FIGS. 10A and B). Although QC and 9AA efficiently suppressed 17-DMAG-activated transcription of the hsp70A1 gene, they had no effect on the levels of several other (non-17-DMAG induced) mRNAs, including those for GAPDH, p65RelA, and GRP94 (FIG. 10C).

QC was also effective in blocking HSR induced by hyperthermia as illustrated in FIG. 10D. In this experiment, the activity of the HSF1 transcription factor, which is known to be essential for induction of hsp70 expression during HSR, was directly assessed. HSF1 reporter cells were generated by infecting HeLa cells with a lentiviral reporter construct containing the EGFP cDNA under the control of an HSF1-responsive promoter. Upon treatment with bortezomib, 17-DMAG or hyperthermia, HSF1-dependent EGFP synthesis was induced, as detected by fluorescent microscopy. Co-treatment of the reporter cells with QC in addition to any of the three different proteotoxic stress inducers blocked EGFP accumulation. The results of this example demonstrate that the anti-malaria drug QC is a powerful inhibitor of HSR.

Example 4

Quinacrine Affects HSF1 Function Downstream of Nuclear Translocation and DNA Binding This example demonstrates that quinacrine affects HSF1 function downstream of nuclear translocation and DNA binding. Activation of HSF1-mediated transcription requires release of HSF1 from its complex with hsp90 in the cytoplasm. This is followed by formation of HSF1 homodimers and homotrimers that translocate into the nucleus and bind to specific HSF1 recognition sites within the promoters of heat shock-inducible genes. The effect of QC and 9AA on this process was studied in order to define the point at which these compounds act to inhibit HSF1 function. To assess the intracellular localization and DNA binding capacity of HSF1 complexes, electrophoretic mobility shift assays (EMSA) were performed using protein extracts purified from the cytoplasm or nuclei of cells subjected to proteotoxic stress alone or in combination with QC or 9AA. The results of these experiments are shown in FIG. 11. Treatment of HeLa cells with MG132, heat shock, or 17-DMAG led to activation of specific HSF1 DNA binding activity in both cytoplasmic (FIG. 11A) and nuclear extracts (FIG. 11B). QC and 9AA did not interfere with or modify the strength of these effects at any concentration tested (up to 100 mM) (data not shown and FIG. 11B). These results indicate that inhibition of HSF1-dependent transcription by QC and 9AA occurs at a point downstream of its cytoplasmic activation, nuclear translocation, and DNA binding.

The finding that QC and 9AA affect HSF1 downstream of its nuclear translocation suggests that the compounds themselves are localized, at least in part, in the nucleus. This is supported by results obtained using experimental modulation of their intracellular distribution. Bafilomycin, a lysosome-targeted antibiotic, can significantly alter the intracellular distribution of lysosome-tropic compounds, including quinacrine and chloroquine, by inhibiting lysosomal H+-ATPase. Treatment of HeLa cells with bafilomycin resulted in a switch in the intracellular localization of QC from predominantly lysosomal to predominantly nuclear (FIG. 11C) as judged by fluorescent microscopy (both QC and 9AA are naturally fluorescent compounds). The affects of bafilomycin treatment on the sensitivity of hsp70 induction to QC were tested. Bafilomycin increased the efficacy of QC as an HSR inhibitor in MG132-treated HeLa cells, as shown in FIG. 11D, In the presence of the antibiotic, 5 mM QC inhibited hsp70 synthesis as effectively as 20 mM QC in the absence of the antibiotic. These results indicate that the inhibitory activity of QC against HSF1-mediated transcription depends on its nuclear concentration.

Example 5

Combination of Quinacrine with Proteotoxic Stress Induces Apoptosis

This example demonstrates that combining quinacrine with proteotoxic stress induces apoptosis. Heat shock response (HSR) is an adaptive pro-survival response that can protect cells from a variety of toxic conditions. Rapid accumulation of inducible forms of chaperones, such as hsp70 and hsp27, has been shown to prevent cell death under conditions of heat shock or treatment with inhibitors of proteasomes or hsp90]. Therefore, the ability of QC and 9AA to prevent induction of proteins encoded by HSF1-responsive genes may greatly increase the cytotoxicity of proteotoxic stresses. HeLa cells were treated with 17-DMAG or bortezomib alone or in combination with QC, and the effects on cell viability and induction of apoptosis were analyzed. As shown in FIGS. 4A and 4B, QC greatly enhanced the toxicity of 17-DMAG and bortezomib, respectively. Combined treatment with concentrations of QC that caused less than a 50% reduction in cell viability and practically non-toxic concentrations of 17-DMAG or bortezomib resulted in a dramatic reduction in the number of growing cells.

Whether induction of apoptosis played a role in the impact of the drug treatments on the number of viable cells was investigated. Apoptosis was monitored by the appearance of caspase-specific cleavage products of keratin 18 and PARP. Consistent with the results of the cell viability assays, combined treatment with QC and either bortezomib or 17-DMAG strongly activated caspase-mediated protein cleavage that was barely detectable when the drugs were used alone (FIGS. 12C and D). The caspase inhibitor ZVAD-FMK blocked this effect completely, indicating that the proteolytic cleavage events were caspase-specific (FIG. 12E).

To address whether inhibition of hsp70 induction plays a critical role in QC-mediated cell sensitization to bortezomib and 17-DMAG, the effect of QC was compared with that of an alternative method of hsp70 suppression. HeLa cells were transfected with siRNA specifically designed against the inducible form of hsp70. The transfected cells were unable to synthesize inducible hsp70 upon treatment with proteasome or hsp90 inhibitors (FIG. 12D). The inability to synthesize hsp70 under conditions of proteotoxic stress activated an apoptotic response similar to that caused by combined treatment with QC and proteotoxic stress inducing agents (FIG. 12D). The similarity of the biological effects of siRNA-mediated knockdown of hsp70 and QC treatment with respect to cell sensitivity to bortezomib and 17-DMAG suggests that the combined toxicity of QC and proteotoxic stress inducers is mediated by suppression of HSR by QC.

Example 6

Anti-Tumor Effect of Combination of Quinacrine with hsp90 Inhibitor

Figure 13:
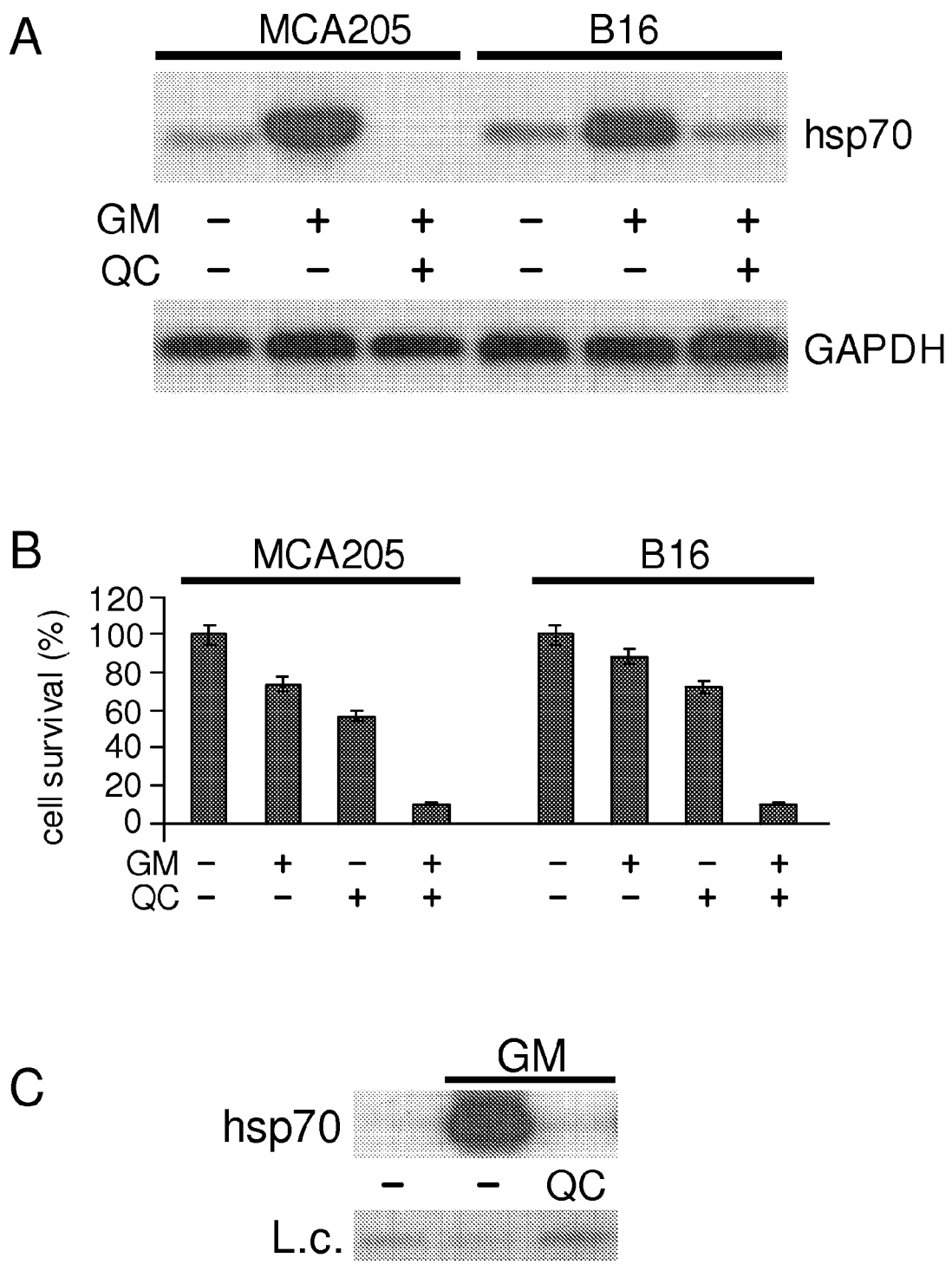
FIG. 13 shows the effect of 17-DMAG and quinacrine on tumor cell growth in vitro and in vivo.
Figure 17:
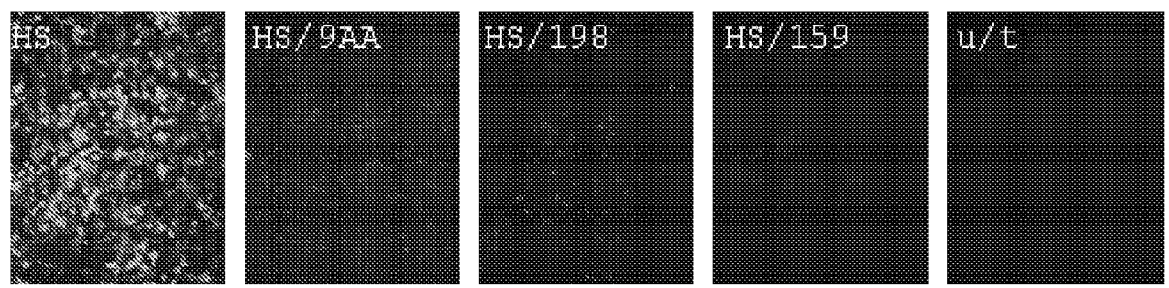
FIG. 17 shows the effects of heat shock (HS) and AA/CRBZ on HSF1-specific GFP expression. HeLa cells infected with HSF1 specific GFP expressing lentivirus were treated with HS at 43° C. for 30 min, or HS in combination with 20 μM of 9AA, or 1 μM of CRBZ 198 or CRBZ 159. u/t—untreated HeLa cells. GFP expression is shown at 12 h of 37° C. recovery.

This example demonstrates that combining quinacrine with a hsp90 inhibitor has anti-tumor effects. The finding that combination of QC with proteotoxic stress-inducing drugs has a strong toxic effect on HeLa cells in vitro suggests that such combinations could have significant potential as anti-cancer therapies. To investigate this possibility, the effect of QC/17-DMAG combination treatment on tumor growth in vivo was tested using two syngeneic mouse tumor models: MCA205 fibrosarcoma and B-16 melanoma. 17-DMAG was used since it is a proteotoxic stress inducer that has shown limited antitumor efficacy as a monotherapy. The effect of 17-DMAG and QC on induction of HSR (FIG. 13A) and cell viability (FIG. 13B) in MCA205 and B-16 cells in vitro was tested. Both cell lines responded to the drugs in a manner similar to HeLa cells, indicating that these models can validly be used to test the antitumor activity of the QC/17-DMAG combination. To confirm that the drugs have a similar effect on HSR induction in tumors growing in vivo, MCA205 cells were implanted in C57BL/6 mice and the resulting tumors were treated with a single intra-tumor injection of PBS (control), 25 mg 17-DMAG alone, or 1.25 mg QC with 25 µg 17-DMAG. Five hours later, mice were sacrificed and RNA prepared from the isolated tumors was analyzed for hsp70 induction. As shown in FIG. 13C, 17-DMAG treatment induced hsp70 synthesis in tumors grown in vivo and QC prevented this induction. To assess the effect of the drug combination on tumor growth in vivo, mice carrying MCA205 (FIG. 13D) or B-16 (FIG. 13E) tumors were treated by intra-tumor injection with QC and 17-DMAG alone or in combination. The size of the tumors was measured regularly (every 2 days) after drug injection. In both experimental models, QC and 17-DMAG applied as single agents had minor antitumor effects (the delay in tumor growth), whereas in combination they completely prevented tumor growth. Tumor sizes were measured up to 24 days after implantation. Tumors with single drug injection started to overgrow the tumors with combinatorial drug injections from day 16 for B-16 cells and from day 18 for MCA205 cells (FIGS. 13A and B). The combined QC/17-DMAG treatment not only prevented tumor growth, but actually led to tumor regression, with tumors shrinking from ~50 mm$^3$ in size to undetectable. These findings indicate that combining QC with proteotoxic stress inducers leads to apoptosis.

Example 7

Methods

1. Cell Culture, Lentiviral Vectors, siRNA Transfection, and Drugs

HeLa cells were cultured in Dulbecco modified Eagle's medium (Invitrogen/Gibco BRL, Carlsbad, Calif.) supplemented with 10% fetal calf serum. Murine melanoma B16 and fibrosarcoma MCA205 cells were grown in complete RPMI-1640 medium supplemented with 2 mM L-glutamine, 100 µg/ml streptomycin, 100 U/ml penicillin, 50 µg/ml Gentamicin (Life Technologies, Grand Island, N.Y.). HSF1-specific EGFP expression was generated by insertion of 6 copies of HSF1 regulatory elements (HSE) 5' CAGAACGTTCTAG 3' (SEQ ID NO: 1) upstream of a minimal CMV promoter into a PTR-mCMV-EGFP lentiviral vector. Cells were infected by lentivirus with MOI 10 in the presence of 4 µg/ml of polybrene overnight. Efficiency of infection was detected by EGFP expression in response to 43° C. for 60 min of heat shock. Between 70 and 90% of the cells were infected by virus and expressed GFP in response to heat shock.

HeLa cells were transfected with hsp70 siRNA (Santa Cruz Biotechnology, Santa Cruz, Calif.) for 24 h to inhibit hsp70 expression during additional treatments with drugs. Control cells were transfected with a non-hsp-70-specific siRNA-A (Santa Cruz Biotechnology, Santa Cruz, Calif.). Cells were treated as described in the text with the proteasome inhibitors MG132 (Calbiochem, San Diego, Calif.) and bortezomib (LC Laboratories, Woburn, Mass.), the hsp90 inhibitor 17-DMAG (LC Laboratories, Woburn, Mass.), quinacrine, emetine, quinine, chloroquine, and 9AA (all from Sigma, St. Louis, Mo.). Hyperthermia/heat shock treatment was performed by incubation at 43° C. for 1 h.

2. Western Immunoblotting

Total protein extracts from HeLa cells were prepared in RIPA buffer (150 mM NaCl, 1% SDS, 10 mM Tris (pH 8.0), 1% sodium deoxycholate, 1% NP-40) containing a protease inhibitor cocktail (Sigma, St. Louis, Mo.). Protein extracts were separated by electrophoresis in 4-20% gradient polyacrylamide gels with SDS (Invitrogen/Novex, Carlsbad, Calif.) and then transferred to nylon PVDF membranes (Amersham, Piscataway, N.J.). Membranes were pre-incubated over-night in 5% milk solution, and then incubated for 1 h in 1% milk solution with primary antibodies at 1:1000 dilutions. The following primary antibodies were used: rabbit anti-hsp70A1 inducible form (Assay Designs/StressGen, Victiria, BC, Canada) and rat anti-HSF1 (Assay Designs/StressGen, Victiria, BC, Canada). Controls for protein loading were rat anti-pirin antibody (Institut für Biochemie der Ludwig-Maximilians-Universität München, Germany) and rabbit anti-keratin 18 antibody (Burnham research Institute, CA). Apoptosis was analyzed by detection of caspase-specific cleavage of K18 (Burnham research Institute, CA) and PARP (antibody from Santa Cruz Biotechnology, Santa Cruz, Calif.). HRP-conjugated secondary anti-rabbit, anti-rat, and anti-mouse antibodies were purchased from Santa Cruz Biotechnology. Detection reagent (ECL) was from Perkin Elmer (Shelton, Conn.).

3. Northern Blotting and Hybridization

Total RNA (10 µg) from HeLa, B-16, or MCA205 cells was analyzed by Northern blot hybridization with probes specific to the hsp70A1, MT1, p65RelA, GRP94, and GAPDH genes. A PCR fragment was generated from the hsp70A1 cDNA (Invitrogen, Carlsbad, Calif.) with primers specific for the hsp70A1 coding sequence (Als: 5' CCA CCA TCC CCA CCA AGC AGA C3' (SEQ ID NO: 2); Ala: 5' CAT GAA CCA TCC TCT CCA CCT 3') (SEQ ID NO: 3). All other hybridization probes were generated by restriction endonuclease digestion from cDNA clones (ORIGENE).

In vivo $^{35}$S-protein labeling. HeLa cells were treated with drugs and their combinations according to the protocols of experiments. The regular culture medium was changed to a methionine/cysteine-free medium supplemented with $^{35}$S-methionine and $^{35}$S-cysteine (50 mCi/ml) (New England Nuclear/Perkin Elmer, Shelton, Conn.) and the cells were incubated for additional 60 min in the presence of drugs. Cytoplasmic protein extracts were prepared according to the Dignam protocol. Labeled proteins were analyzed by electrophoresis in 10% polyacrilimide gel and autoradiography.

4. In Vitro Assay for Proteasome Activity

To determine the efficiency of the proteasome inhibitors MG132 and Bortezomib alone and in combination with QC and 9AA, we treated HeLa cells with the indicated drugs for 4 h, purified cytoplasmic protein extracts, and analyzed proteasome activity using fluorochromic proteasome substrate 1 (Calbiochem, San Diego, Calif.).

5. Electrophoretic Mobility Shift Assay (EMSA)

HSF1 DNA binding activity was detected using EMSA. Briefly, cytoplasmic and nuclear protein extracts were purified using the Digman protocol from control HeLa cells and HeLa cells treated with MG132 or 17-DMAG alone, or in combination with QC or 9AA. 10 µg of protein extracts were analyzed with a $^{32}$P-labeled double-stranded oligonucleotide (5' TCG-AGC-TAG-AAG-CTT-CTA-GAA-GCT-TCT-AGC 3') (SEQ ID NO: 4) specific for HSF1 binding. For the competition assay, a 50× excess of unlabeled oligonucleotides was added to protein extracts together with $^{32}$P-labeled double-stranded oligonucleotides. Protein extracts were pre-incubated with HSF1 specific antibodies (Assay Designs/StressGen, Victoria, BC, Canada) for 15 min at room temperature before adding $^{32}$P-labeled double-stranded oligonucleotide to perform the super shift assay.

6. Cell Viability Assay

To determine the cytotoxicity of drugs and drug combinations, a cell viability assay was used. Cells were grown to 75-80% confluency and then treated for 4 h with various combinations of 1 mM 17-DMAG, 0.1 mM bortezomib and 10 mM or 20 mM QC. Cells were collected by trypsinization and a 1:50 dilution was seeded in a 6-well plate. Cell viability was determined 72 h later by methylene blue staining after fixing the cells with 10% formaldehyde. Methylene blue was extracted by 0.1M HCl and its absorbance was measured at 560 nm.

7. In Vivo Assay for Tumor Growth in Mice

MCA205 and B-16 cells were detached from plastic Petri dishes using 0.5% Trypsin-EDTA, washed and resuspended in sterile PBS. Cells were injected intra-dermally into the shaved abdominal area of C57BL/6 mice ($3\times10^5$ cells in a single injection/mouse). Tumors were measured in two dimensions and tumor volume was calculated according to the formula: mm$^3$=tumor length×(tumor width). On day 8 after implantation, tumors were typically ~50 mm$^3$ in size. Tumor-bearing mice were divided into four groups of five animals each and began receiving intra-tumor drug injections on day 9. The control group received PBS injections on days 9, 10, 11, and 12. Mice in group 2 were injected with 1.25 mg QC in PBS on days 9 and 10. Mice in group 3 received 25 µg 17-DMAG in PBS on days 9, 10, 11, and 12. Mice in group 4 were injected with 1.25 mg QC+25 µg 17-DMAG on days 9 and 10, and 25 µg 17-DMAG on days 11 and 12. Only two injections of QC were given, because this drug is stable inside of cells. It may be detected in cells as long as 72 h after treatment and the change of medium. Tumors were measured every 2 days after drugs injections for 24 days. Animals with tumors volume 500 mm3 and larger were euthanized.

Example 8

Figure 14:
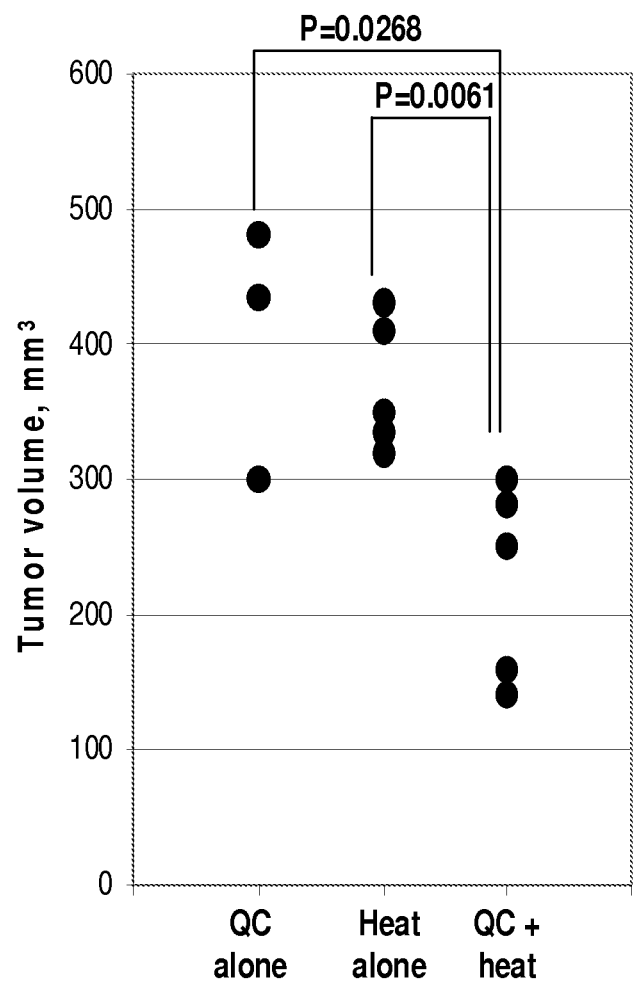
FIG. 14 shows the anti-tumor effects in a mouse model of combined non-efficacious doses of quinacrine and local hyperthermia.

Combination of Non-Efficacious Doses of Quinacrine and Local Hyperthermia Provide Anti-Tumor Effect in Mouse Model This example shows that combined non-efficacious doses of quinacrine and local hyperthermia have anti-tumor effects in a mouse model. S.c. tumors formed by C26 mouse colon carcinoma were grown in syngeneic Balb/c mice. When tumors reached 50-150 mm$^3$, mice were treated by per oral administration of quinacrine (500 mg/kg), or local hyperthermia (1 hour –41.5° C.) or combination of both (quinacrine was given 2 hours before hyperthermia). Five days later tumors were measured and these results are shown in FIG. 14 with the calculation of statistical significance of observed differences. Combinational treatment showed clear advantage in terms of antitumor effect as compared to each treatment applied separately.

Example 9

CRBZ Prevents Expression of hsp70 in Response to Proteotoxic Stress (PS)

Figure 15:
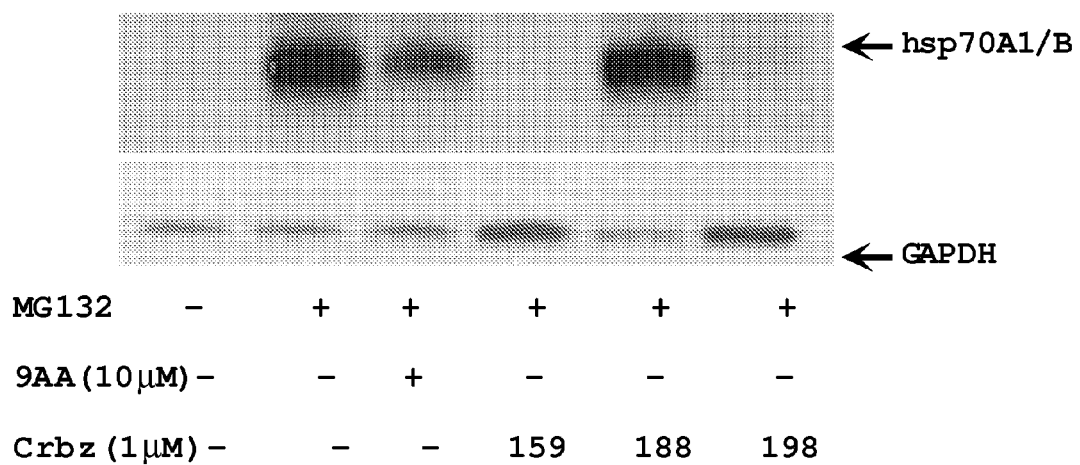
FIG. 15 shows the effects of CRBZ on hsp70 gene expression in response to PS, as indicated by Northern hybridization of RNA from control HeLa cells, cells treated for 5 h with MG132, and combinations of MG132 with 10 μM of 9AA, or 1 μM of CRBZ (Crbz) 159, 188, and 198 with probe for hsp70A1/B genes. GAPDH is a loading control.
Figure 16:
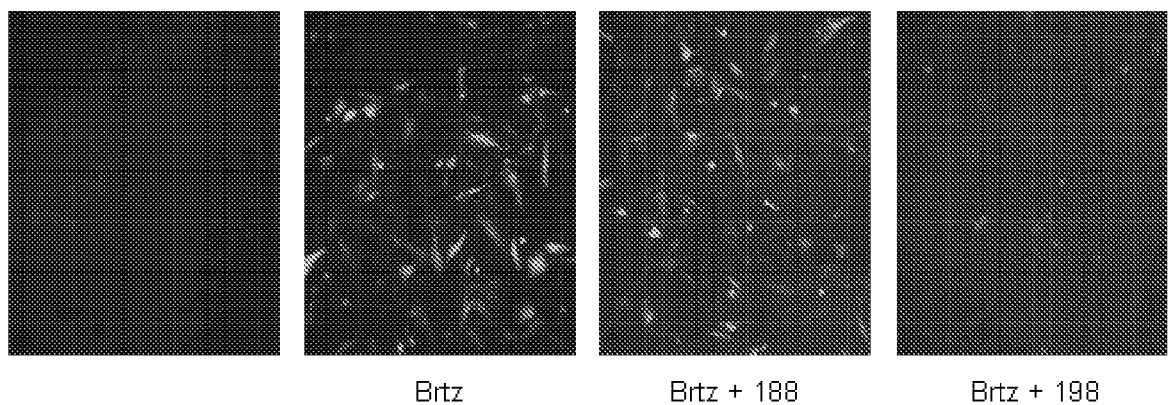
FIG. 16 shows that CRBZ 198 affects HSF1-specific expression of GFP reporter. Reporter gene expressing lentivirus infected HeLa cells were treated with 0.1 μM of Bortezomib (Brtz) alone and in combination with 1 μM of CRBZ 188 (inactive), or CRBZ 198 (active). Expression of GFP was analyzed microscopically 10 h after treatment.

This example shows that a carbazole can prevent hsp70 expression in response to proteotoxic stress (PS). Although aminoacridines (AA) efficiently suppresses expression of hsp70 in response to different inducers of PS, specific activity of these compounds is not high. They are active in micro molar concentrations. To find chemicals with better abilities than AA, compounds with structure similar to AA were analyzed. To verify the ability of carbazoles (CRBZ) to affect hsp70 expression in response to PS, cells were treated with MG132 and variable amounts of several CRBZ and analyzed the expression of hsp70 by Northern blotting. CRBZ numbers 159 and 198 were active in these assays. Selected compounds 159 and 198 were active at concentrations starting from 1 μM (FIG. 15). CRBZ 198 efficiently inhibited the HSF1-specific expression of GFP in cells treated with Bortezomib (FIG. 16), and CRBZ 159 and 198 were active in inhibition of expression of GFP reporter in response to hyperthermia (FIG. 17). Thus, CRBZ may increase the toxicity of PS with a better therapeutic index than AA.

The invention claimed is:

1. A method for inducing cell death, comprising: (a) inhibiting adaptive heat shock response in a cell; and (b) inducing heat shock response in the cell, wherein the inhibitor of the adaptive heat shock response is a carbazole selected from the group consisting of CBL0137, CBL0197, CBL0198, CBL0100, CBL0159, CBL0212, CBL0174, and CBL0175.

2. The method of claim 1, wherein heat shock response is induced by administering a heat shock-inducing agent to the cell.

3. The method of claim 2, wherein the heat shock-inducing agent is geldanamycin, a proteasome inhibitor, an aresenite compound, or ethanol.

4. The method of claim 3, wherein the proteasome inhibitor is bortezomib.

5. The method of claim 1, wherein heat shock response is induced by increasing the internal temperature of the cell.

6. The method of claim 5, wherein the temperature is increased with a heating means.

7. The method of claim 1, wherein the cell is a cancer cell.

8. The method of claim 7, wherein the cancer is selected from the group consisting of: metastatic breast cancer, bladder cancer, lung carcinoma, esophageal cancer, basal cell carcinoma, malignant melanoma, ocular tumor, and head and neck cancer.

9. The method of claim 1, wherein a second treatment is co-administered with inducing heat shock response in the cell.

10. The method of claim 9, wherein the second treatment comprises an anti-cancer agent.

11. The method of claim 6, wherein the temperature is increased to at least 39-60° C.

12. The method of claim 6, wherein the temperature is increased with infrared radiation.

13. The method of claim 12, wherein the radiation is of a wavelength of 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 μm.

14. The method of claim 6, wherein the temperature is increased with a heat source selected from the group consisting of: an electroluminescent device, a laser diode, a vertical cavity surface emitting laser, a light emitting diode, and a resistive filament lamp.

* * * * *

UNITED STATES PATENT AND TRADEMARK OFFICE
CERTIFICATE OF CORRECTION

| | | |
|---|---|---|
| PATENT NO. | : 8,486,697 B2 | Page 1 of 1 |
| APPLICATION NO. | : 12/993018 | |
| DATED | : July 16, 2013 | |
| INVENTOR(S) | : Gudkov et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 330 days.

Signed and Sealed this
Eleventh Day of November, 2014

Michelle K. Lee
*Deputy Director of the United States Patent and Trademark Office*